(12) United States Patent
Katoh et al.

(10) Patent No.: US 9,464,228 B2
(45) Date of Patent: Oct. 11, 2016

(54) LIQUID CRYSTAL COMPOSITION, METHOD FOR MANUFACTURING THE SAME, AND FILM

(71) Applicant: FUJIFILM Corporation, Tokyo (JP)

(72) Inventors: Shunya Katoh, Kanagawa (JP); Hiroshi Matsuyama, Kanagawa (JP); Masaru Yoshikawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/661,771

(22) Filed: Mar. 18, 2015

(65) Prior Publication Data

US 2015/0191652 A1    Jul. 9, 2015

Related U.S. Application Data

(63) Continuation of application No. PCT/JP2013/073284, filed on Aug. 30, 2013.

(30) Foreign Application Priority Data

Sep. 25, 2012 (JP) ................. 2012-210376
Mar. 14, 2013 (JP) ................. 2013-051318
Aug. 22, 2013 (JP) ................. 2013-172608

(51) Int. Cl.

| C09K 19/20 | (2006.01) |
|---|---|
| C09K 19/54 | (2006.01) |
| C09K 19/38 | (2006.01) |
| C09K 19/34 | (2006.01) |
| C09K 19/46 | (2006.01) |
| C07C 235/56 | (2006.01) |
| G02B 5/30 | (2006.01) |
| C07C 327/28 | (2006.01) |
| C07C 251/24 | (2006.01) |
| C07C 251/88 | (2006.01) |
| C08F 220/30 | (2006.01) |
| C09K 19/04 | (2006.01) |
| C08F 222/10 | (2006.01) |

(52) U.S. Cl.
CPC ......... C09K 19/2007 (2013.01); C07C 235/56 (2013.01); C07C 251/24 (2013.01); C07C 251/88 (2013.01); C07C 327/28 (2013.01); C09K 19/3444 (2013.01); C09K 19/3475 (2013.01); C09K 19/46 (2013.01); G02B 5/3016 (2013.01); C08F 220/30 (2013.01); C08F 222/1006 (2013.01); C09K 19/54 (2013.01); C09K 2019/044 (2013.01); C09K 2019/0448 (2013.01); C09K 2019/2035 (2013.01); C09K 2019/2078 (2013.01)

(58) Field of Classification Search
CPC .............. C09K 19/46; C09K 19/2007; C09K 19/3444; C09K 19/3475; C09K 19/54; C09K 2019/044; C09K 2019/0448; C09K 2019/2078; C09K 2019/2035; G02B 5/3016
See application file for complete search history.

(56) References Cited

U.S. PATENT DOCUMENTS

| 7,157,124 B2 | 1/2007 | Sasada et al. |
| 8,568,839 B2 | 10/2013 | Takeuchi et al. |
| 2004/0222403 A1 | 11/2004 | Sasada et al. |
| 2008/0143943 A1* | 6/2008 | May ................ C09K 19/18 349/117 |
| 2010/0078593 A1 | 4/2010 | Takeuchi et al. |
| 2014/0192286 A1* | 7/2014 | Tasaka ............. C09K 19/2007 349/16 |

FOREIGN PATENT DOCUMENTS

| JP | 2001-521538 A | 11/2001 |
| JP | 2004-231638 A | 8/2004 |
| JP | 2010-083947 A | 4/2010 |
| KR | 10-2001-0012086 A | 2/2001 |
| WO | 96/04351 A1 | 2/1996 |

OTHER PUBLICATIONS

Official Action issued by the Japanese Patent Office (JPO) on Jun. 9, 2015 in connection with Japanese Patent Application No. 2013-172608.
International Search Report issued in PCT/JP2013/073284 on Dec. 3, 2013.
Written Opinion issued in PCT/JP2013/073284 on Dec. 3, 2013.
International Preliminary Report on Patentability issued by WIPO on Apr. 9, 2015 in connection with Intl. Patent Application No. PCT/JP2013/073284.
Notice of Grounds for Rejection issued by the Korean Intellectual Property Office on Jun. 3, 2016, in connection with Korean Patent Application No. 2015-7006710.

* cited by examiner

*Primary Examiner* — Shean C Wu
(74) *Attorney, Agent, or Firm* — Jean C. Edwards, Esq.; Edwards Neils LLC

(57) ABSTRACT

A method for manufacturing a liquid crystal composition, the method including concurrently obtaining a liquid crystal compound represented by the formula (I) and a liquid crystal compound represented by the formula (II), by allowing a compound represented by the formula (III) to react with a carboxylic acid represented by the formula (IV) and a carboxylic acid represented by the formula (V), wherein $P^1$ represents a polymerizable group; $Sp^1$ represents a $C_{3-12}$ divalent aliphatic group, etc; $T^1$ represents a 1,4-phenylene group; $T^2$ represents a divalent group having a single bond or cyclic structure; $A^1$ represents —COO—, etc; $A^2$ and $A^3$ represents —OCO—, etc; X represents a hydrogen atom, $C_{1-12}$ alkyl group, etc; $Y^1$ and $Y^2$ represents O, $NR^1$ or S; $R^1$ represents a hydrogen atom or methyl group; Formula (I) $P^1$-$Sp^1$-$T^1$-$A^1$-B-$A^2$-$T^1$-$Sp^1$-$P^1$; Formula (II) $P^1$-$Sp^1$-$T^1$-$A^1$-B-$A^3$-$T^2$-X; Formula (III) being $HY^1$—B—$Y^2$H; Formula (IV) $P^1$-$Sp^1$-$T^1$-COOH; Formula (V) X-$T^2$-COOH.

11 Claims, 1 Drawing Sheet

The upper is for Example 1 and the lower is for Comparative Example 1.

The upper is for Example 6 and the lower is for Comparative Example 2.

LIQUID CRYSTAL COMPOSITION, METHOD FOR MANUFACTURING THE SAME, AND FILM

CROSS-REFERENCE TO RELATED APPLICATIONS

This application is a Continuation of PCT International Application No. PCT/JP2013/073284, which was published under PCT article 21(2) in Japanese, filed on Aug. 30, 2013, which claims priority under 35 U.S.C § 119(a) to Japanese Patent Application No. 2012-210376 filed on Sep. 25, 2012, Japanese Patent Application No. 2013-051318 filed on Mar. 14, 2013, and Japanese Patent Application No. 2013-172608 filed on Aug. 22, 2013. The above applications are hereby expressly incorporated by reference, in their entirety, into the present application.

TECHNICAL FIELD

The present invention relates to a liquid crystal composition versatile for various applications represented by various optical components including optically anisotropic film and heat barrier film, a method for manufacturing the same, and a film using the liquid crystal composition.

BACKGROUND ART

Polymerizable liquid crystal used for fabricating optically anisotropic film has suffered from that it often crystallizes in the process of coating or after dried.

As a countermeasure, it has been known that mixing of a target polymerizable liquid crystal with other polymerizable liquid crystal successfully suppressed the crystallization. Known examples of suppressing the crystallization include use of a composition which contains a (meth)acrylate compound having two (meth)acryloyl groups on the molecular terminal together with the other polymerizable liquid crystal compound; and use of a composition prepared, in the process of manufacture, as a random mixture of polymerizable liquid crystals having a (meth)acryloyl group and an alkyl group on both molecular terminals. The method, however, showed only limited degrees of suppressive effect on crystallization.

As a method for manufacturing a liquid crystal composition containing two or more species of polymerizable liquid crystals, there have been reported methods for manufacturing a liquid crystal composition containing two or more species of polymerizable liquid crystals all at once, using two or more species of raw materials. For example, Patent Literature 1 describes a method for synthesizing a liquid crystal mixture containing two or more species of polymerizable liquid crystals, using a compound having a hydroxy group or derivative of the a compound having a hydroxy group, and a nucleophilic compound having a non-carboxyl-type leaving group and a polymerizable group. The method is reportedly successful in manufacturing the liquid crystal composition with a high liquid crystallinity, in a time-saving and cost-saving manner. Patent Literature 2 describes a method for manufacturing a composition containing two or more species of polymerizable liquid crystals, by allowing a compound having hydroxy group and so forth, to react with a compound having a carboxyl group derivative and a polymerizable group.

CITATION LIST

[Patent Literature 1] Japanese Translation of PCT International Application Publication No. JP-T2-2001-521538
[Patent Literature 2] International Patent WO96/04351

SUMMARY OF THE INVENTION

Technical Problem

The methods described in Patent Literatures 1 or 2 were, however, not satisfactory in terms of economy and performances of the resultant compositions. In addition, Patent Literature 1 described a single synthetic method (making a core first, and then attaching side chains), which was only capable of producing a mixed composition having a limited range of bonding styles of the side chains and the core. Also Patent Literature 2 did not describe a method for manufacturing a liquid crystal composition, such as synthesizing all at once a monofunctional polymerizable liquid crystal having a single polymerizable group, and a bifunctional polymerizable liquid crystal having two polymerizable groups. Also there was no suggestion on a method for manufacturing such liquid crystal composition.

A problem to be solved by this invention relates to provide a method for manufacturing, all at once, a liquid crystal composition by using two or more different species of carboxylic acids as one part of the raw material, wherein the liquid crystal composition has high levels of crystallization suppressive performance, solubility and liquid crystallinity.

Solution to Problem

After intensive studies aimed at solving the above-described problems, the present inventors found out that a liquid crystal composition having high levels of crystallization suppressive performance, solubility and liquid crystallinity may be manufactured all at once, by using, as raw materials, two or more different species of carboxylic acids having a specific structure (the carboxylic acid having polymerizable groups and the carboxylic acid not having any polymerizable group) and a hydroquinone having a specific structure, and by allowing the materials to react to each other.

The present invention aimed to solve the above-described problem is as described below:

[1] A method for manufacturing a liquid crystal composition, the method comprising concurrently obtaining a liquid crystal compound represented by the formula (I) below and a liquid crystal compound represented by the formula (II) below, by allowing a compound represented by the formula (III) below to react with a carboxylic acid represented by the formula (IV) below and a carboxylic acid represented by the formula (V) below;

| | |
|---|---|
| $P^1\text{-Sp}^1\text{-T}^1\text{-A}^1\text{-B-A}^2\text{-T}^1\text{-Sp}^1\text{-P}^1$ | Formula (I) |
| $P^1\text{-Sp}^1\text{-T}^1\text{-A}^1\text{-B-A}^3\text{-T}^2\text{-X}$ | Formula (II) |
| $HY^1\text{—B—}Y^2H$ | Formula (III) |
| $P^1\text{-Sp}^1\text{-T}^1\text{-COOH}$ | Formula (IV) |
| $X\text{-T}^2\text{-COOH}$ | Formula (V) |

(wherein,

P$^1$ represents a polymerizable group;

Sp$^1$ represents a C$_{3-12}$ divalent aliphatic group which may have a substituent, and one CH$_2$ or two or more non-adjacent (CH$_2$)s in the aliphatic group may be substituted by —O—, —S—, —OCO—, —COO— or —OCOO—;

T$^1$ represents a 1,4-phenylene group;

T$^2$ represents a divalent group having a single bond or cyclic structure;

A$^1$ represents —COO—, —CONR$^1$— (R$^1$ represents a hydrogen atom or methyl group) or —COS—;

Each of A$^2$ and A$^3$ independently represents —OCO—, —NR$^1$CO— (R$^1$ represents a hydrogen atom or methyl group) or —SCO—;

B represents a divalent group having a cyclic structure which may have a substituent;

X represents a hydrogen atom, branched or straight-chain C$_{1-12}$ alkyl group, branched or straight-chain C$_{1-12}$ alkoxy group, phenyl group, cyano group, halogen atom, nitro group, acetyl group, vinyl group, formyl group, —OC(=O)R (R represents a C$_{1-12}$ alkyl group), N-acetylamide group, acryloylamino group, N,N-dimethylamino group, N-maleimide group, methacryloylamino group, aryloxy group, N-alkyloxycarbamoyl group having a C$_{1-4}$ alkyl group, allyloxycarbamoyl group, N-(2-methacryloyloxy-ethyl)carbamoyloxy group, N-(2-acryloyloxyethyl)carbamoyloxy group or a structure represented by the Formula (V-I) below;

Each of Y$^1$ and Y$^2$ independently represents O, NR$^1$ (R$^1$ represents a hydrogen atom or methyl group) or S;)

-A$^4$-T$^4$-Sp$^2$-P$^2$   Formula (V-I)

(wherein, P$^2$ represents a polymerizable group or hydrogen atom, and each of A$^4$, T$^4$ and Sp$^2$ are independently the same as A$^2$, T$^2$ and Sp$^1$.)

[2] The method for manufacturing a liquid crystal composition of [1], wherein in the formulae (I) to (V), X represents a hydrogen atom, branched or straight-chain C$_{1-12}$ alkyl group, branched or straight-chain C$_{1-12}$ alkoxy group, phenyl group, cyano group, halogen atom, nitro group, acetyl group or vinyl group.

[3] The method for manufacturing a liquid crystal composition of [1] or [2], further comprising;

activating the carboxylic acid represented by the formula (IV) and the carboxylic acid represented by the formula (V), by converting them into a mixed acid anhydride or acid halide, wherein subsequent to the activating, the compound represented by the formula (III) is allowed to react with the activated carboxylic acid represented by the formula (IV) and the activated carboxylic acid represented by the formula (V), in the presence of a base.

[4] The method for manufacturing a liquid crystal composition of any one of [1] to [3], wherein feed ratio by mole of the carboxylic acid represented by the formula (IV) and the carboxylic acid represented by the formula (V) falls in the range from 75:25 to 99:1.

[5] The method for manufacturing a liquid crystal composition of any one of [1] to [4], wherein production ratio by mole of the compound represented by the formula (I) and the compound represented by the formula (II) falls in the range from 50:50 to 98:2.

[6] The method for manufacturing a liquid crystal composition of any one of [1] to [5], wherein compositional ratio by mass of the compound represented by the formula (I) and the compound represented by the formula (II), in the liquid crystal composition, falls in the range from 50:50 to 95:5.

[7] The method for manufacturing a liquid crystal composition of any one of [1] to [6], wherein B represents any one linking group selected from the group (VI) consisting of the linking groups below;

[Chemical Formula 1]
Group (VI) of Linking Groups

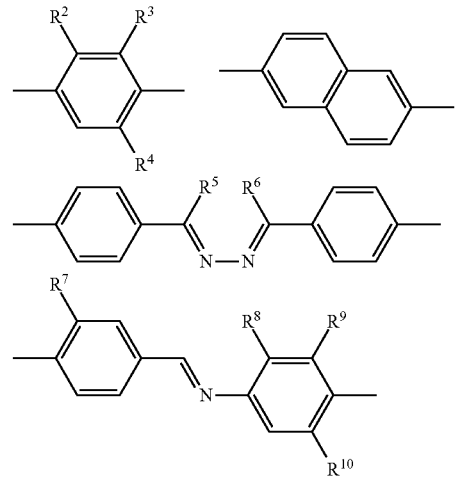

(wherein, each of R$^2$ to R$^{10}$ independently represents a hydrogen atom, branched or straight-chain C$_{1-4}$ alkyl group, branched or straight-chain C$_{1-4}$ alkoxy group, halogen atom, or, C$_{1-3}$ alkoxycarbonyl group.)

[8] The method for manufacturing a liquid crystal composition of any one of [1] to [7], wherein T$^2$ represents any one linking group selected from the group (VII) consisting of the linking groups below;

[Chemical Formula 2]
Group (VII) of Linking Groups

[9] The method for manufacturing a liquid crystal composition of any one of [1] to [8], wherein B represents any one linking group selected from the group (VIII) consisting of the linking groups below;

[Chemical Formula 3]
Group (VIII) of Linking Groups

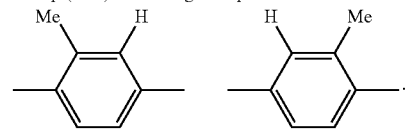

[10] The method for manufacturing a liquid crystal composition of any one of [1] to [9], wherein X represents a branched or straight-chain C$_{1-4}$ alkyl group, straight-chain C$_1$ or C$_2$ alkoxy group, or, phenyl group.

[11] The method for manufacturing a liquid crystal composition of any one of [1] to [10], wherein
each of $Y^1$ and $Y^2$ represents O,
$A^1$ represents —COO—, and
each of $A^2$ and $A^3$ represents —OCO—.
[12] A liquid crystal composition manufactured by a method for manufacturing a liquid crystal composition described in any one of [1] to [11].
[13] A film comprising an optically anisotropic layer obtained by fixing alignment of the liquid crystal compounds in a liquid crystal composition described in [12].
[14] The film of [13], wherein the optically anisotropic layer is obtained by fixing cholesteric alignment of the liquid crystal compounds.
[15] The film of [14], showing a selective reflection characteristic.
[16] The film of [14] or [15], showing selective reflection characteristic in the infrared wavelength region.
[17] The film of [13], wherein the optically anisotropic layer is obtained by fixing homogeneous alignment of the liquid crystal compounds.
[18] The film of [13], wherein the optically anisotropic layer is obtained by fixing homeotropic alignment of the liquid crystal compounds.
[19] A polarizing plate comprising a film described in [17] or [18], and a polarizing film.
[20] A liquid crystal display device comprising a polarizing plate described in [19].

Advantageous Effects of Invention

According to the present invention, successfully provided is a method for manufacturing, all at once, a liquid crystal composition having high levels of crystallization suppressive performance, solubility and liquid crystallinity, by using two or more different species of carboxylic acids as one part of the raw material.

DESCRIPTION OF EMBODIMENTS

Figure 1:
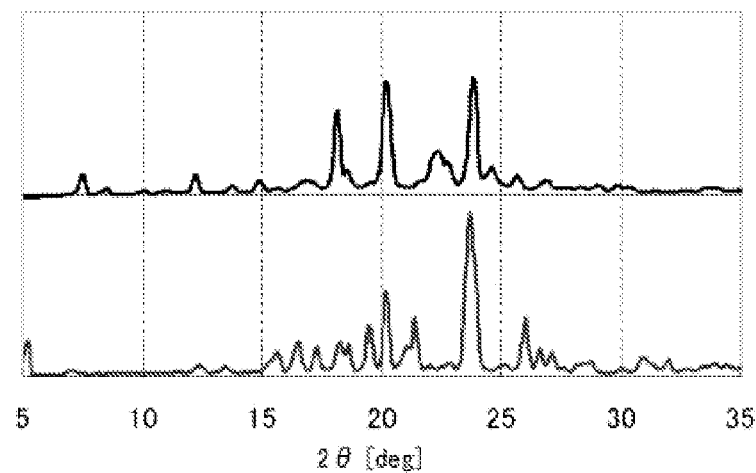
FIG. 1 An X-ray diffraction spectral chart of a liquid crystalline composition of Example 1 and a liquid crystalline composition of Comparative Example 1.

The present invention will be detailed below. Explanation of constituent features will occasionally be made on representative embodiments or specific examples of the present invention, to which the present invention by no means limited. In the present specification, all numerical ranges expressed using "to" with preceding and succeeding numerals are defined to contain these numerals as the lower and upper limit values.
[Method for Manufacturing Liquid Crystal Composition]

According to the present invention, there is provided a method for manufacturing a liquid crystal composition of the present invention, the method includes concurrently obtaining a liquid crystal compound represented by the formula (I) below and a liquid crystal compound represented by the formula (II) below, by allowing a compound represented by the formula (III) below to react with a carboxylic acid represented by the formula (IV) below and a carboxylic acid represented by the formula (V) below:

$P^1\text{-}Sp^1\text{-}T^1\text{-}A^1\text{-}B\text{-}A^2\text{-}T^1Sp^1\text{-}P^1$  Formula (I)

$P^1\text{-}Sp^1\text{-}T^1\text{-}A^1\text{-}B\text{-}A^3\text{-}T^2\text{-}X$  Formula (II)

$HY^1\text{—}B\text{—}Y^2H$  Formula (III)

$P^1\text{-}Sp^1T^1\text{-}COOH$  Formula (IV)

$X\text{-}T^2\text{-}COOH$  Formula (V)

(in the formulae (I) to (V), $P^1$ represents a polymerizable group. $Sp^1$ represents a $C_{3\text{-}12}$ divalent aliphatic group which may have a substituent, and one $CH_2$ or two or more non-adjacent $(CH_2)$s in the aliphatic group may be substituted by —O—, —S—, —OCO—, —COO— or —OCOO—. $T^1$ represents a 1,4-phenylene group. $T^2$ represents a divalent group having a single bond or cyclic structure. $A^1$ represents —COO—, —CONR$^1$— ($R^1$ represents a hydrogen atom or methyl group) or —COS—. Each of $A^2$ and $A^3$ independently represents —OCO—, —NR$^1$CO— ($R^1$ represents a hydrogen atom or methyl group) or —SCO—. B represents a divalent group having a cyclic structure which may have a substituent.

X represents a hydrogen atom, branched or straight-chain $C_{1\text{-}12}$ alkyl group, branched or straight-chain $C_{1\text{-}12}$ alkoxy group, phenyl group, cyano group, halogen atom, nitro group, acetyl group, vinyl group, formyl group, —OC(=O)R (R represents a $C_{1\text{-}12}$ alkyl group), N-acetylamide group, acryloylamino group, N,N-dimethylamino group, N-maleimide group, methacryloylamino group, aryloxy group, N-alkyloxycarbamoyl group having a $C_{1\text{-}4}$ alkyl group, allyloxycarbamoyl group, N-(2-methacryloyloxyethyl)carbamoyloxy group, N-(2-acryloyloxyethyl)carbamoyloxy group or a structure represented by the Formula (V-I) below. Each of $Y^1$ and $Y^2$ independently represents O, NR$^1$ ($R^1$ represents a hydrogen atom or methyl group) or S.)

$\text{-}A^4\text{-}T^4\text{-}Sp^2\text{-}P^2$  Formula (V-I)

(in the formula (V-I), $P^2$ represents a polymerizable group or hydrogen atom, and each of $A^4$, $T^4$ and $Sp^2$ are independently the same as $A^2$, $T^2$ and $Sp^1$.)

With this configuration, it is now possible to provide a method for manufacturing, all at once, a liquid crystal composition having high levels of crystallization suppressive performance, solubility and liquid crystallinity, by using two or more different species of carboxylic acids as one part of the raw material.
<Synthetic Scheme, Order of Synthesis, Reaction Conditions>

To "concurrently" obtain the liquid crystal compound represented by the formula (I) and the liquid crystal compound represented by the formula (II) is not necessarily limited to that both liquid crystal compounds are synthesized exactly at the same time, but means that the liquid crystal compound represented by the formula (I) and the liquid crystal compound represented by the formula (II) are obtained by allowing the compound represented by the formula (III) to react with the carboxylic acid represented by the formula (IV) and the carboxylic acid represented by the formula (V) by one-pot synthesis.

An exemplary synthetic scheme of the method for manufacturing a liquid crystal composition of the present invention is shown below. In the present specification, compounds (I) to (V) are represented by the formulae (I) to (V) above, respectively.

Synthetic Scheme

[Chemical Formula 4]

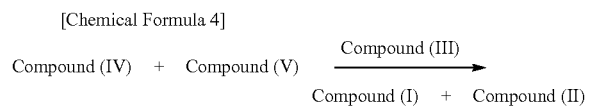

In the method for manufacturing a liquid crystal composition of the present invention, the order of synthesis may be other than that represented by the scheme above, without special limitation.

The order of addition of the carboxylic acid represented by the formula (IV) and the carboxylic acid represented by the formula (V) is not specifically limited.

It is preferable that the method for manufacturing a liquid crystal composition of the present invention further include a step of activating the carboxylic acid represented by the formula (IV) and the carboxylic acid represented by the formula (V), by converting them into a mixed acid anhydride or acid halide, wherein, subsequent to the activating, the compound represented by the formula (III) is allowed to react with the activated carboxylic acid represented by the formula (IV) and the activated carboxylic acid represented by the formula (V), in the presence of a base.

An activating agent usable for the activating is exemplified by methanesulfonyl chloride and toluenesulfonyl chloride, without special limitation. The base usable here is exemplified by tertiary amine (for example, triethylamine, diisopropylethylamine), and inorganic salt, without special limitation. The activating is preferably proceeded under cooling on ice.

From the viewpoint of avoiding that the compound represented by the formula (III) is adversely affected by the activating agent, it is preferable to add the compound represented by the formula (III) subsequent to the activating. Subsequent to the activating, it is preferable to add the compound represented by the formula (III), to the activated carboxylic acid represented by the formula (IV) and the activated carboxylic acid represented by the formula (V), in the presence of a base, under cooling on ice. Condition under which the compound represented by the formula (III) is allowed to react with the activated carboxylic acid represented by the formula (IV) and the activated carboxylic acid represented by the formula (V) is preferably 0 to 30° C., and more preferably 10 to 25° C., but not specifically limited thereto.

<Compound Represented by Formula (III)>

The method for manufacturing a liquid crystal composition of the present invention uses the compound represented by the formula (III) below, as one raw material.

$HY^1$—B—$Y^2H$  Formula (III)

In the formula (III), B represents a divalent group having a cyclic structure which may have a substituent. Each of $Y^1$ and $Y^2$ independently represents O, $NR^1$ ($R^1$ represents a hydrogen atom or methyl group) or S.

B represents a divalent group having a cyclic structure which may have a substituent, and is preferably any one linking group selected from the group (VI) consisting of the linking groups below:

[Chemical Formula 5]
Group (VI) of Linking Groups

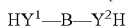
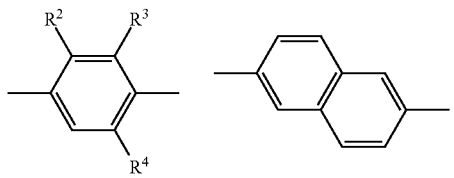
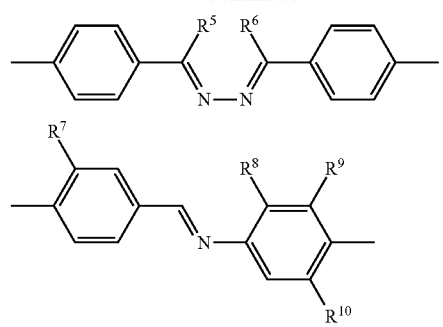

In the group (VI) of linking groups, each of $R^2$ to $R^{10}$ independently represents a hydrogen atom, branched or straight-chain $C_{1-4}$ alkyl group, branched or straight-chain $C_{1-4}$ alkoxy group, halogen atom, or, $C_{1-3}$ alkoxycarbonyl group.

It is more preferable that each of $R^2$ to $R^{10}$ independently represents a hydrogen atom, branched or straight-chain $C_{1-4}$ alkyl group. Hydrogen atom and straight-chain $C_1$ or $C_2$ alkyl group are particularly preferable.

It is particularly preferable that B represents any one linking group contained in the group (VIII) of linking groups below:

[Chemical Formula 6]
Group (VIII) of Linking Groups

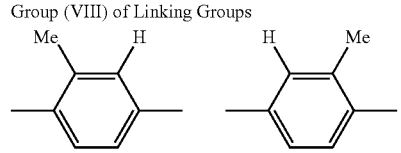

Each of $Y^1$ and $Y^2$ independently represents O, $NR^1$ ($R^1$ represents a hydrogen atom or methyl group) or S, and preferably represents O.

Examples of the compound represented by the formula (III) will be shown below, without limiting the present invention.

[Chemical Formula 7]

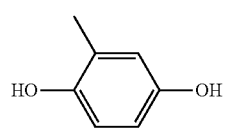
(III-1)

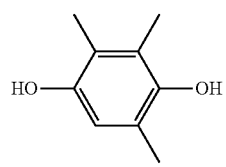
(III-2)

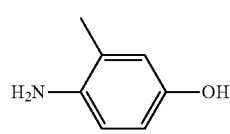
(III-3)

-continued (III-4) 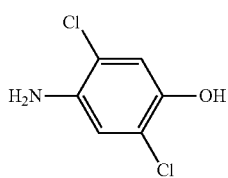

(III-5) 

(III-6) 

(III-7) 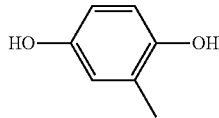

(III-8) 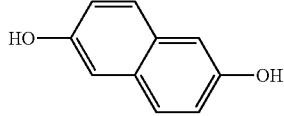

(III-9) 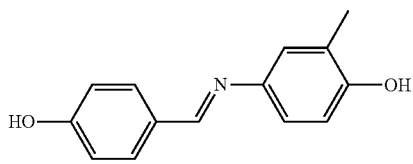

(III-10) 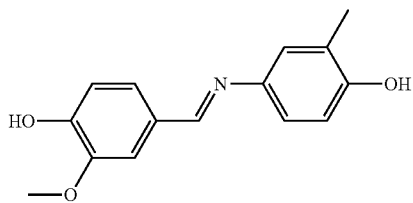

(III-11) 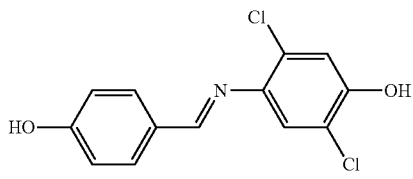

(III-12) 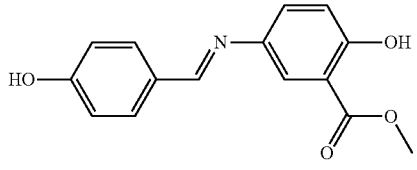

(III-13) 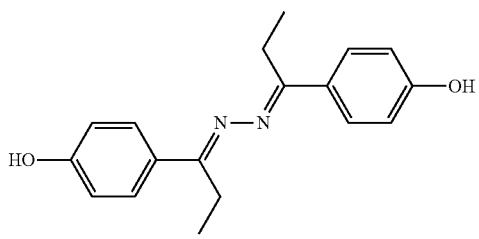

-continued (III-14) 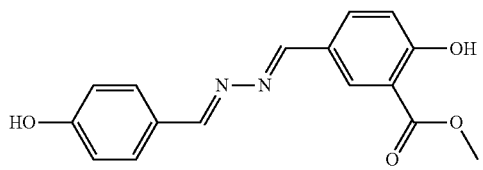

<Carboxylic Acid Represented by Formula (IV)>

The method for manufacturing a liquid crystal composition of the present invention uses the carboxylic acid represented by the formula (IV) below, as one part of the raw materials.

$$P^1\text{-}Sp^1\text{-}T^1\text{-}COOH \qquad \text{Formula (IV)}$$

In the formula (IV), $P^1$ represents a polymerizable group. $Sp^1$ represents a $C_{3-12}$ divalent aliphatic group which may have a substituent, and one $CH_2$ or two or more non-adjacent ($CH_2$)s in the aliphatic group may be substituted by —O—, —S—, —OCO—, —COO— or —OCOO—. $T^1$ represents a 1,4-phenylene group.

$P^1$ represents a polymerizable group. The polymerizable group is not specifically limited, so that details and preferable ranges of the polymerizable group may be referred to paragraphs [0161] to [0171] of JP-A-2002-129162. $P^1$ preferably represents an ethylenic unsaturated double bond group, more preferably a methacryloyl group or acryloyl group, and particularly an acryloyl group.

$Sp^1$ represents a $C_{3-12}$ divalent aliphatic group which may have a substituent, and one $CH_2$ or two or more non-adjacent ($CH_2$)s in the aliphatic group may be substituted by —O—, —S—, —OCO—, —COO— or —OCOO—.

$Sp^1$ represents a $C_{3-12}$ divalent alkylene group which may have a substituent, more preferably represents a $C_{3-8}$ alkylene group, and more preferably furthermore preferably represents a $C_{3-6}$ alkylene group, wherein non-adjacent methylene groups in the alkylene group may be substituted by —O—. While the alkylene group may be branched or not, preferable is non-branched, straight-chain alkylene group.

Examples of the carboxylic acid represented by the formula (IV) will be shown below, without limiting the the present invention.

[Chemical Formula 8]

(IV-1) 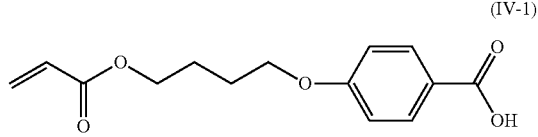

(IV-2) 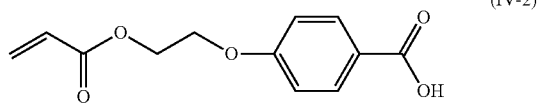

(IV-3) 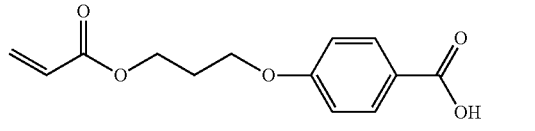

-continued

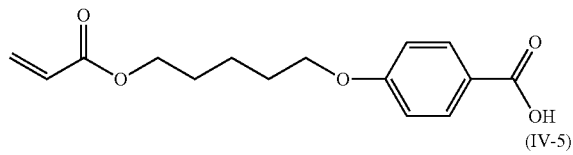

(IV-4)
(IV-5)
(IV-6)
(IV-7)
(IV-8)
(IV-9)
(IV-10)

<Carboxylic Acid Represented by Formula (V)>

The method for manufacturing a liquid crystal composition of the present invention uses the carboxylic acid represented by the formula (V) below, as a part of the raw materials.

X-T²-COOH      Formula (V)

In the formula (V), $T^2$ represents a divalent group having a single bond or cyclic structure. X represents a hydrogen atom, branched or straight-chain $C_{1-12}$ alkyl group, branched or straight-chain $C_{1-12}$ alkoxy group, phenyl group, cyano group, halogen atom, nitro group, acetyl group, vinyl group, formyl group, —OC(=O)R (R represents a $C_{1-12}$ alkyl group), N-acetylamide group, acryloylamino group, N,N-dimethylamino group, N-maleimide group, methacryloylamino group, aryloxy group, N-alkyloxycarbamoyl group having a $C_{1-4}$ alkyl group, allyloxycarbamoyl group, N-(2-methacryloyloxyethyl)carbamoyloxy group, N-(2-acryloyloxyethyl)carbamoyloxy group or a structure represented by the Formula (V-I) below:

-A⁴-T⁴-Sp²-P²      Formula (V-I)

(in the formula (V-I), $P^2$ represents a polymerizable group or hydrogen atom, and each of $A^4$, $T^4$ and $Sp^2$ are independently the same as $A^2$, $T^2$ and $T^2$ represents a divalent group having a single bond or cyclic structure, preferably represents a divalent group having a single bond or divalent aromatic hydrocarbon group or divalent heterocyclic group, and more preferably represents a divalent aromatic hydrocarbon group or divalent heterocyclic group.

The aromatic hydrocarbon group preferably has 6 to 22 carbon atoms, more preferably 6 to 14 carbon atoms, more preferably 6 to 10 carbon atoms, and furthermore preferably 6 carbon atoms. The divalent aromatic hydrocarbon group, configured to have six carbon atoms, preferably has possible bonds at the meta positions or para positions, and particularly at the para positions.

The divalent heterocyclic group preferably has a five-membered, six-membered or seven-membered heterocycle. Five-membered ring or six-membered ring is more preferable, and six-membered ring is most preferable. Heteroatom composing the heterocycle is preferably nitrogen atom, oxygen atom or sulfur atom. The heterocycle is preferably an aromatic heterocycle. The aromatic heterocycle is generally an unsaturated heterocycle. The unsaturated heterocycle is more preferably an unsaturated heterocycle having as much double bonds as possible. Examples of the heterocycle include furan ring, thiophene ring, pyrrole ring, pyrroline ring, pyrrolidine ring, oxazole ring, isoxazole ring, triazole ring, isothiazole ring, imidazole ring, imidazoline ring, imidasolidine ring, pyrazole ring, pyrazoline ring, pyrazolidine ring, triazole ring, furazan ring, tetrazole ring, pyran ring, thiin ring, pyridine ring, piperidine ring, oxazine ring, morpholine ring, thiazine ring, pyridazine ring, pyrimidine ring, pyrazine ring, piperazine ring and trazine ring.

The divalent aromatic hydrocarbon group or divalent heterocyclic group may further have a divalent linking group. The divalent linking group is preferably a $C_{2-4}$ alkenyl group, and more preferably a $C_2$ alkenyl group.

In the method for manufacturing a liquid crystal composition of the present invention, $T^2$ preferably represents any one linking group contained in the group (VII) of linking groups below:

[Chemical Formula 9]
Group (VII) of Linking Groups

X represents a hydrogen atom, branched or straight-chain $C_{1-12}$ alkyl group, branched or straight-chain $C_{1-12}$ alkoxy group, phenyl group, cyano group, halogen atom, nitro group, acetyl group or vinyl group, preferably represents a hydrogen atom, branched or straight-chain $C_{1-4}$ alkyl group, straight-chain $C_1$ or $C_2$ alkoxy group or phenyl group, furthermore preferably represents a branched or straight-chain $C_{1-4}$ alkyl group, straight-chain $C_1$ or $C_2$ alkoxy group or phenyl group, and particularly represents a straight-chain $C_{1-4}$ alkyl group or phenyl group.

X represents a formyl group, acetoxy group, N-acetylamide group, acryloylamino group, N,N-dimethylamino group, N-maleimide group, methacryloylamino group, aryloxy group, N-alkyloxycarbamoyl group having $C_{1-4}$ alkyl group, allyloxycarbamoyl group, N-(2-methacryloyloxyethyl)carbamoyloxy group, N-(2-acryloyloxyethyl)carbamoyloxy group or a structure represented by the Formula (V-I) above.

Among them, acryloylamino group, methacryloylamino group, aryloxy group, allyloxycarbamoyl group, or a structure represented by the Formula (V-I) are preferable, and acryloylamino group, methacryloylamino group or a structure represented by the Formula (V-I) are more preferable.

In the formula (V-I), $P^2$ represents a polymerizable group or hydrogen atom, and preferably represents a polymerizable group. Preferable ranges of the polymerizable group are the same as those of $P^1$. Each of $A^4$, $T^4$ and $Sp^2$ are independently the same as $A^2$, $T^2$ and $Sp^1$, associated with the same preferable ranges.

As for the formula (V-I), it is most preferable that $P^2$ represents a methacryloyl group or acryloyl group, $Sp^2$ represents a $C_{1-12}$ divalent non-branched alkylene group, one $CH_2$ or two or more non-adjacent $(CH_2)$s in the alkylene group may be substituted by —O—, —OCO—, —COO— or —OCOO—, $T^4$ represents a 1,4-phenylene group, and $A^4$ represents —OCO—.

Examples of the carboxylic acid represented by the formula (V) will be shown below, without limiting the present invention.

[Chemical Formula 10]

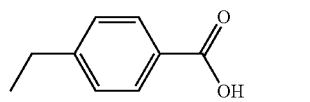
(V-1)

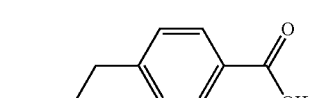
(V-2)

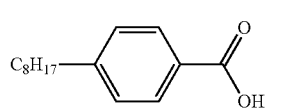
(V-3)

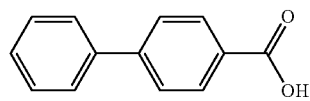
(V-4)

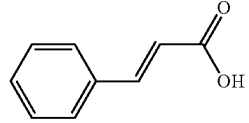
(V-5)

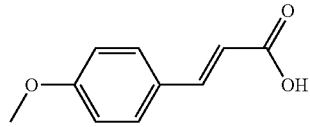
(V-6)

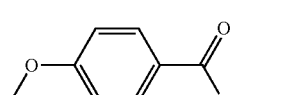
(V-7)

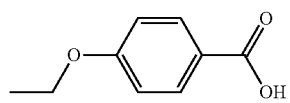
(V-8)

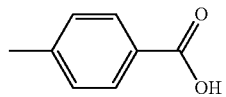
(V-9)

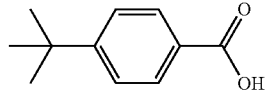
(V-10)

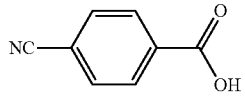
(V-11)

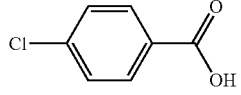
(V-12)

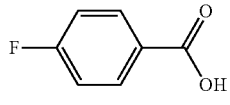
(V-13)

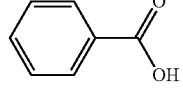
(V-14)

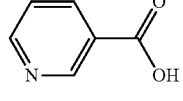
(V-15)

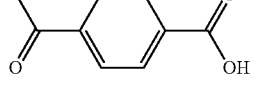
(V-16)

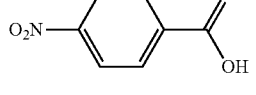
(V-17)

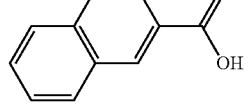
(V-18)

[Chemical Formula 11]

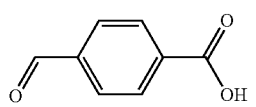
(V-19)

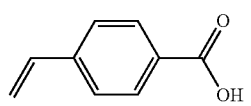
(V-20)

(V-21)

(V-22) 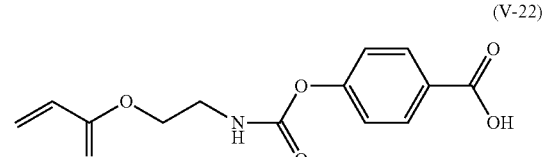

(V-23) 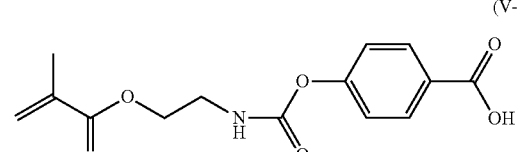

(V-24) 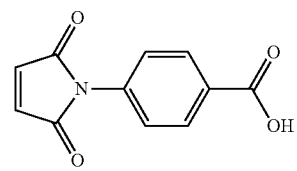

(V-25) 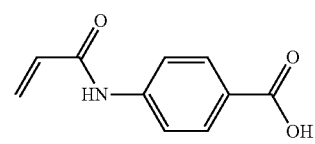

(V-26) 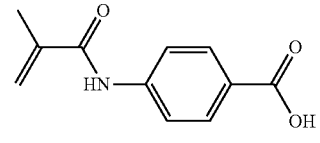

(V-27) 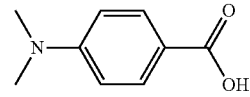

(V-28) 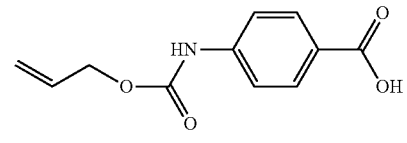

(V-29) 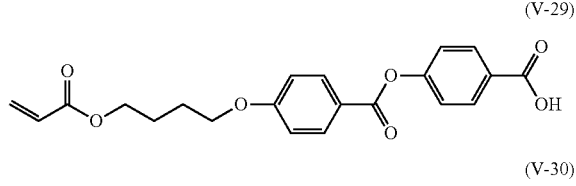

(V-30) 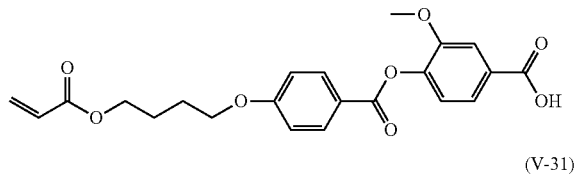

(V-31) 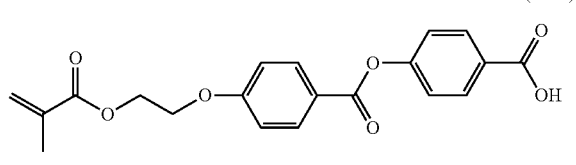

(V-32) 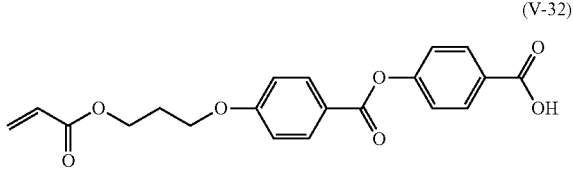

(V-33) 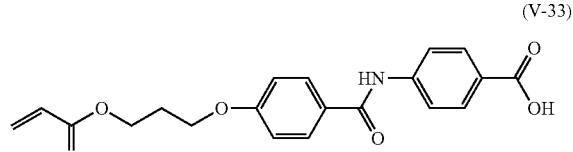

(V-34) 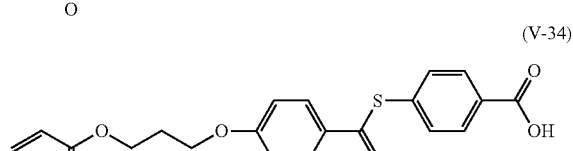

(V-35) 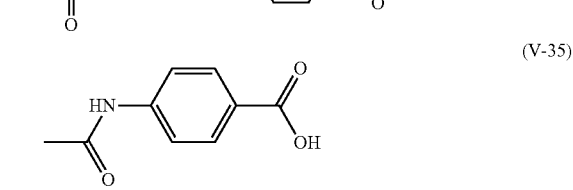

(V-36) 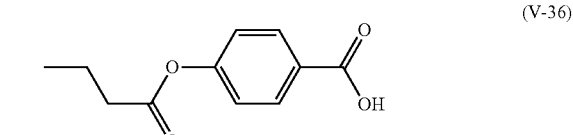

(V-37) 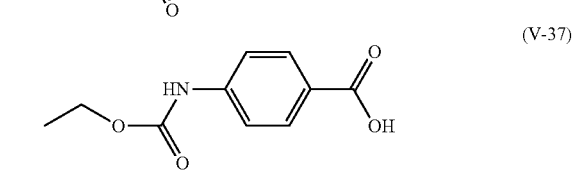

In the method for manufacturing a liquid crystal composition of the present invention, feed ratio by mole of the carboxylic acid represented by the formula (IV) and the carboxylic acid represented by the formula (V) preferably falls in the range from 75:25 to 99:1, more preferably from 77:33 to 95:5, and particularly from 80:20 to 90:10.

<Liquid Crystal Compound Represented by Formula (I) and Compound Represented by Formula (II)>

The method for manufacturing a liquid crystal composition of the present invention is characterized in that the liquid crystal compound represented by the formula (I) below and the liquid crystal compound represented by the formula (II) below are obtained concurrently.

$$P^1\text{-}Sp^1\text{-}T^1\text{-}A^1\text{-}B\text{-}A^2\text{-}T^1\text{-}Sp^1\text{-}P^1 \quad \text{Formula (I)}$$

$$P^1\text{-}Sp^1\text{-}T^1\text{-}A^1\text{-}B\text{-}A^3\text{-}T^2\text{-}X \quad \text{Formula (II)}$$

In the formula (I) and (II), $P^1$ represents a polymerizable group. $Sp^1$ represents a $C_{3\text{-}12}$ divalent aliphatic group which may have a substituent, one $CH_2$ or two or more non-adjacent ($CH_2$)s in the aliphatic group may be substituted by —O—, —S—, —OCO—, —COO— or —OCOO—. $T^1$ represents a 1,4-phenylene group. $T^2$ represents a divalent group having a single bond or cyclic structure. $A^1$ represents —COO—, —CONR$^1$— ($R^1$ represents a hydrogen atom or methyl group) or —COS—. Each of $A^2$ and $A^3$ independently represents —OCO—, —NR$^1$CO— ($R^1$ represents a hydrogen atom or methyl group) or —SCO—. B represents a divalent group having a cyclic structure which may have a substituent.

X represents a hydrogen atom, branched or straight-chain $C_{1-12}$ alkyl group, branched or straight-chain $C_{1-12}$ alkoxy group, phenyl group, cyano group, halogen atom, nitro group, acetyl group, vinyl group, formyl group, —OC(=O)R (R represents a $C_{1-12}$ alkyl group), N-acetylamide group, acryloylamino group, N,N-dimethylamino group, N-maleimide group, methacryloylamino group, aryloxy group, N-alkyloxycarbamoyl group having a $C_{1-4}$ alkyl group, allyloxycarbamoyl group, N-(2-methacryloyloxyethyl)carbamoyloxy group, N-(2-acryloyloxyethyl)carbamoyloxy group or a structure represented by the formula (V-I) above.

Preferable ranges of $P^1$, $Sp^1$, $T^2$, B and X in the formulae (I) and (II) are same as preferable ranges of $P^1$, $Sp^1$, $T^2$, B and X in the formulae (III) to (V).

In the formulae (I) and (II), $A^1$ represents —COO—, —CONR$^1$— ($R^1$ represents a hydrogen atom or methyl group) or —COS—, and preferably represents —COO—.

In the formulae (I) and (II), each of $A^2$ and $A^3$ independently represents —OCO—, —NR$^1$CO— ($R^1$ represents a hydrogen atom or methyl group) or —SCO—, and more preferably represents —OCO—.

It is particularly preferable that, in the formulae (I) and (II), $A^1$ represents —COO—, and, each of $A^2$ and $A^3$ represents —OCO—.

Specific examples of the compound represented by the formula (I) will be shown below, without limiting the present invention.

[Chemical Formula 12]

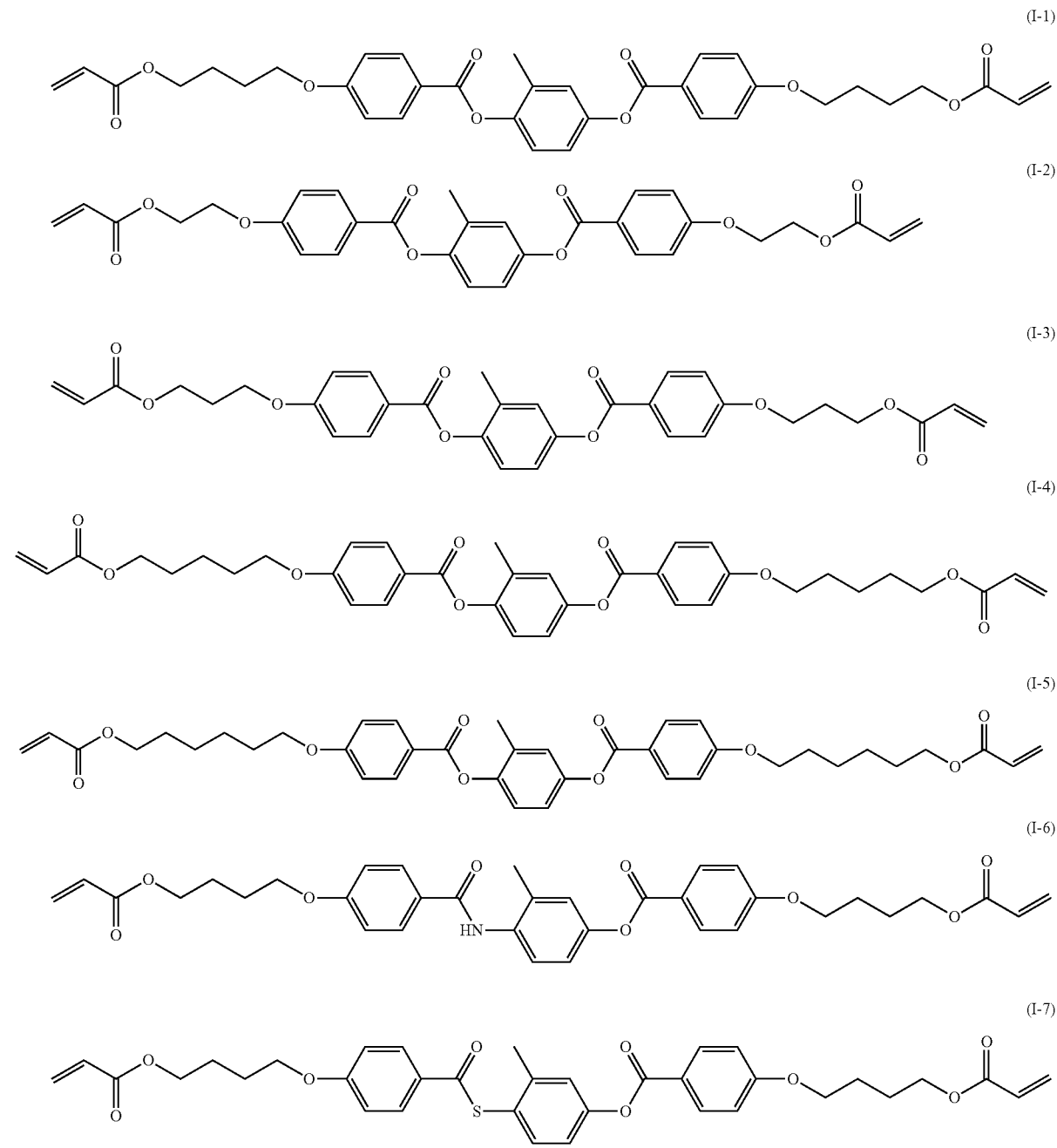

-continued
(I-8)
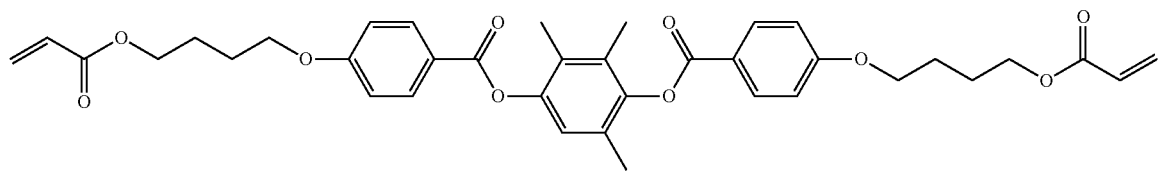
(I-9)
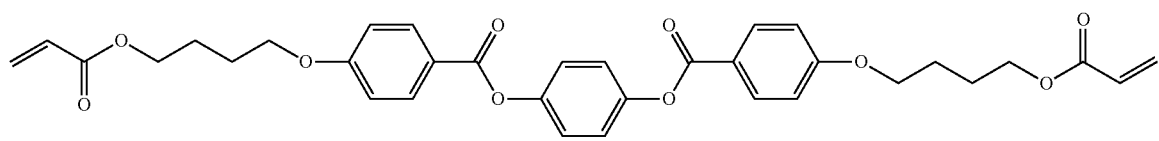
[Chemical Formula 13]
(I-10)
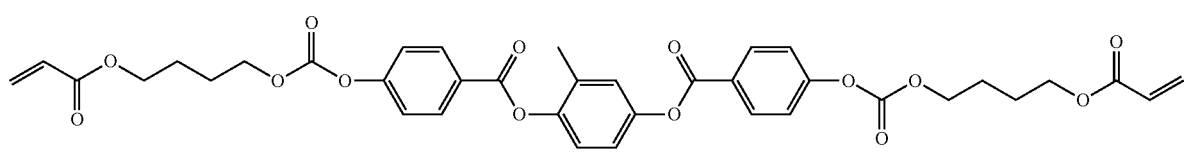
(I-11)
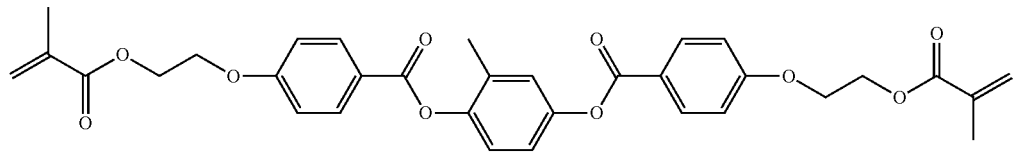
(I-12)
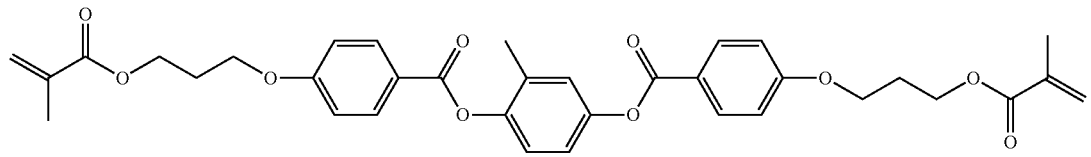
(I-13)
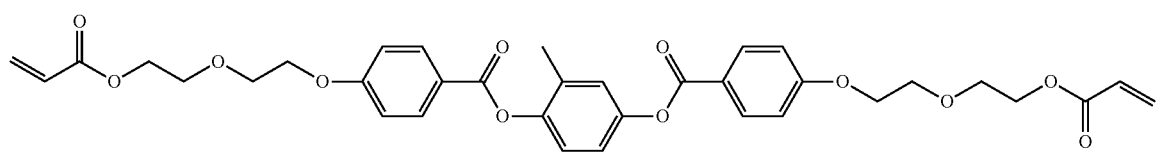
(I-14)
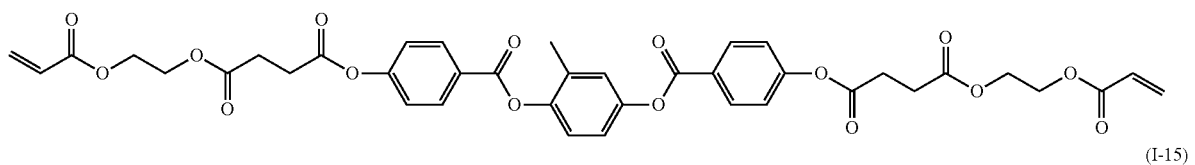
(I-15)
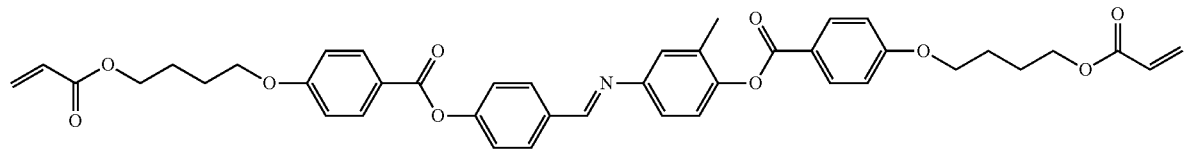
(I-16)
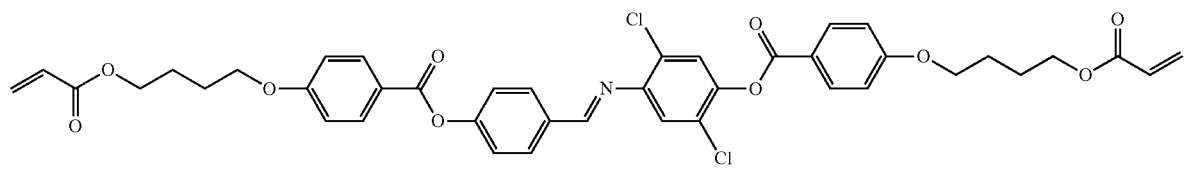

(I-17)
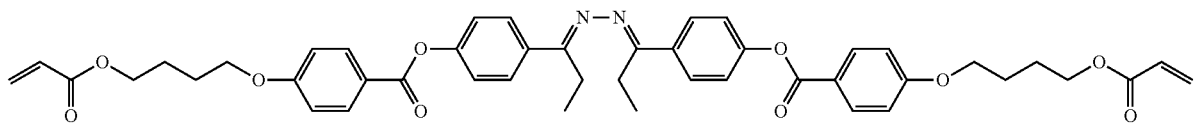
(I-18)
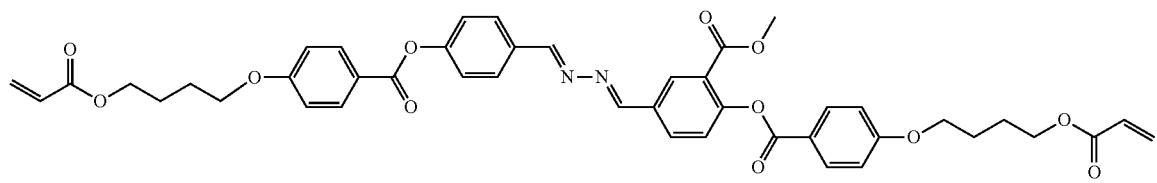
Examples of the compound represented by the formula (II) will be shown below, without limiting the present invention.
[Chemical Formula 14]
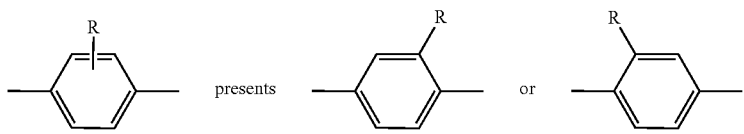
(II-1)
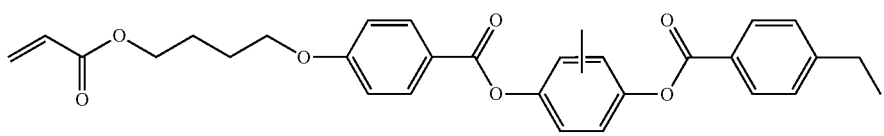
(II-2)
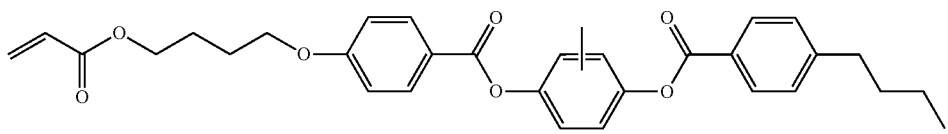
(II-3)
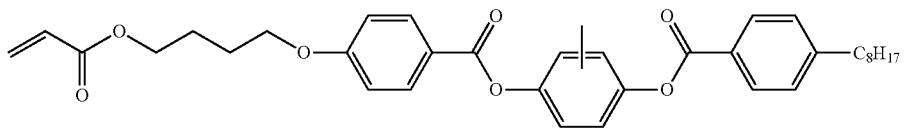
(II-4)
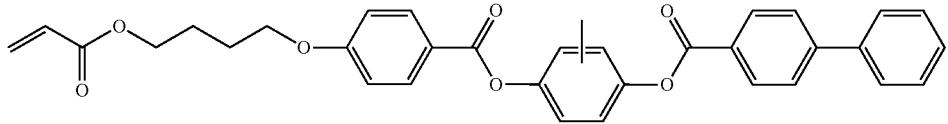
(II-5)
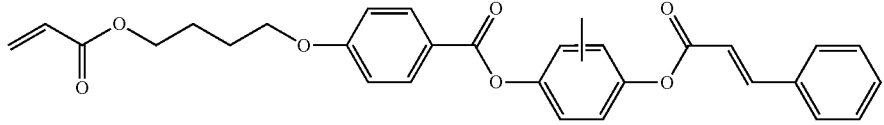
(II-6)
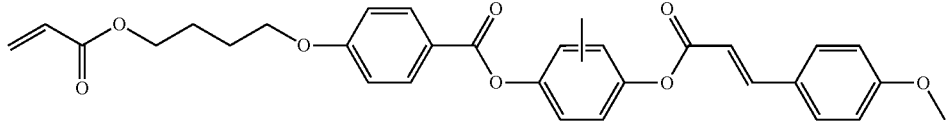

-continued
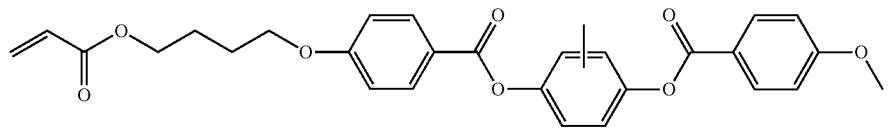
(II-7)
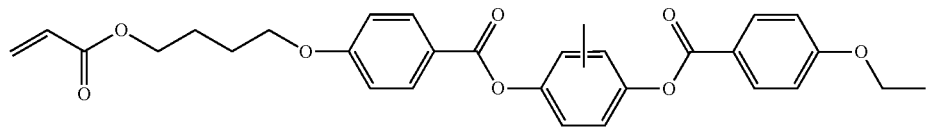
(II-8)
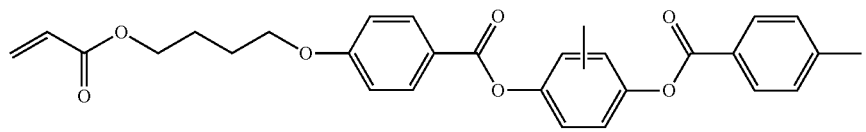
(II-9)
[Chemical Formula 15]
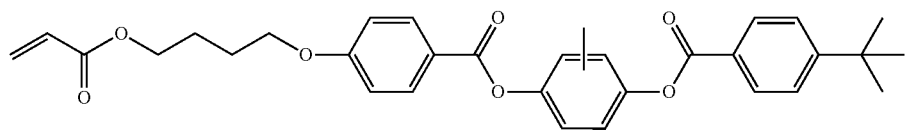
(II-10)
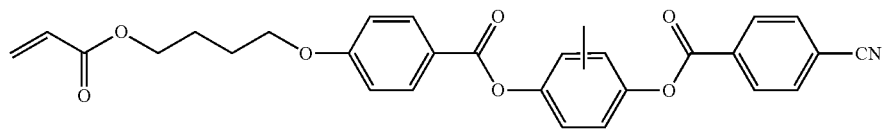
(II-11)
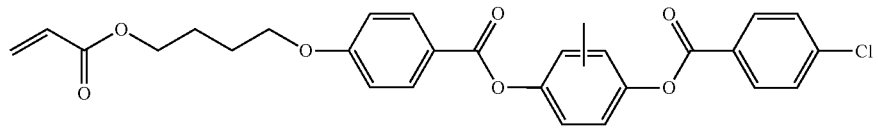
(II-12)
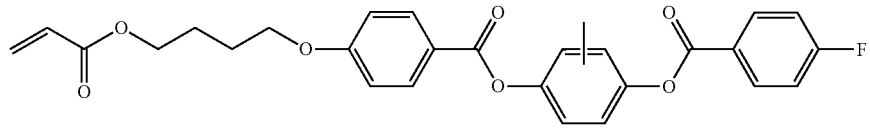
(II-13)
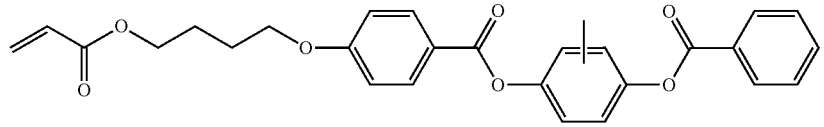
(II-14)
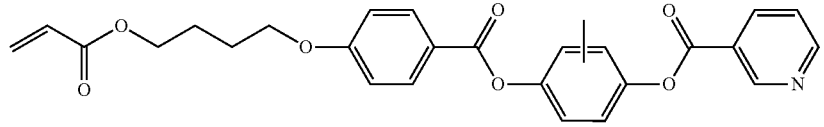
(II-15)
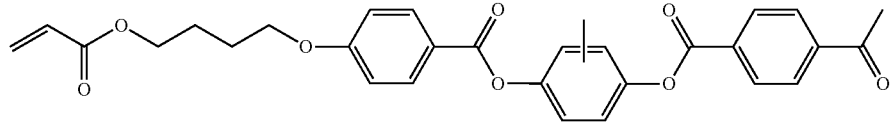
(II-16)
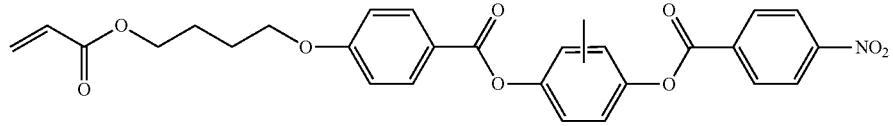
(II-17)

(II-18)
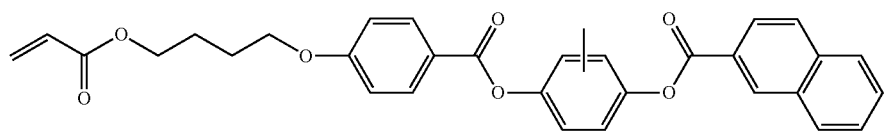
[Chemical Formula 16]
(II-19)
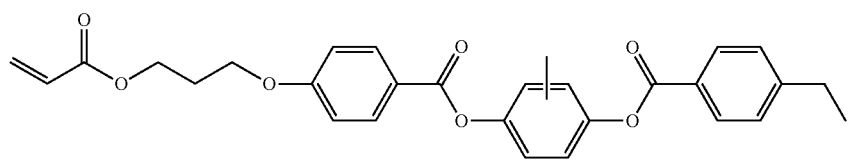
(II-20)
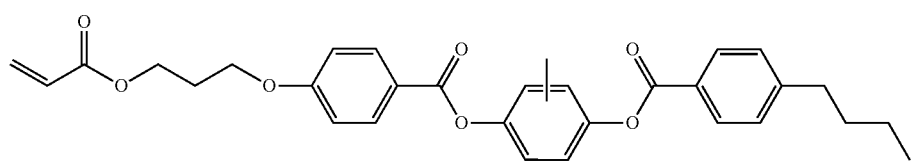
(II-21)
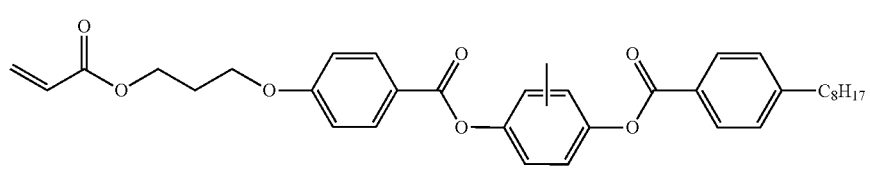
(II-22)
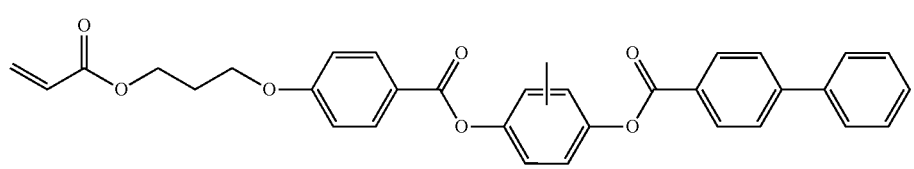
(II-22)
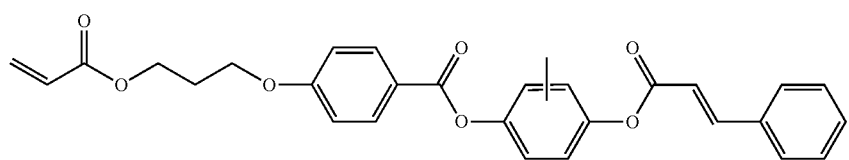
(II-23)
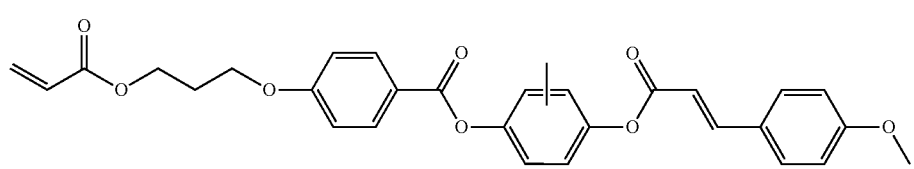
(II-24)
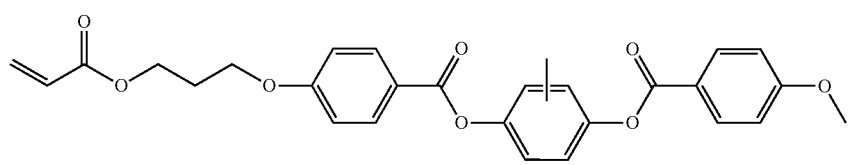
(II-25)
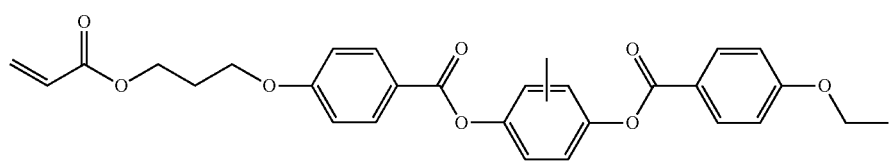

(II-26)
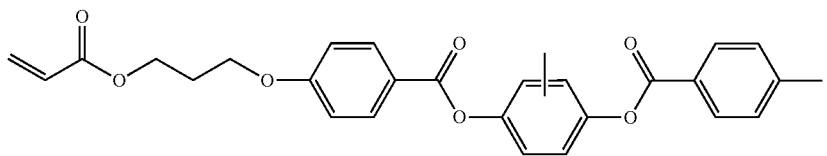
[Chemical Formula 17]
(II-27)
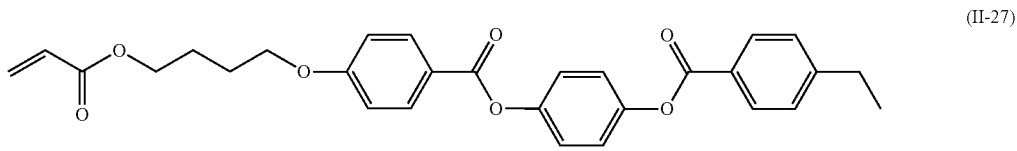
(II-28)
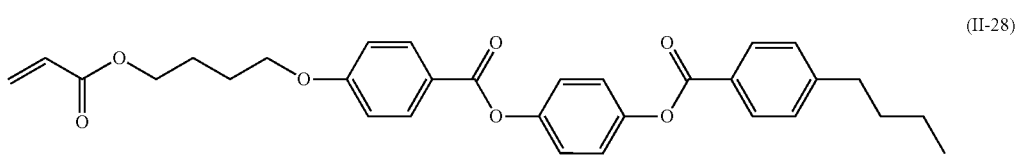
(II-29)
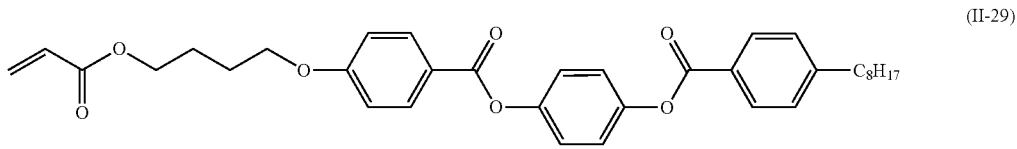
(II-30)
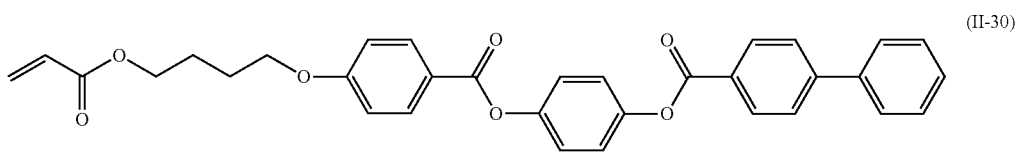
(II-31)
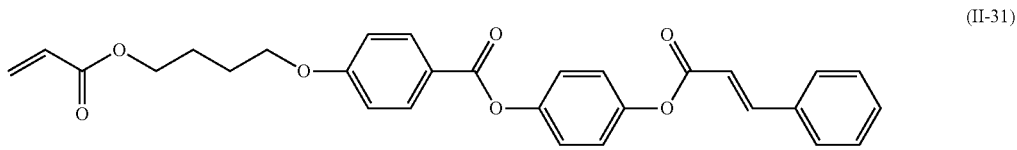
(II-32)
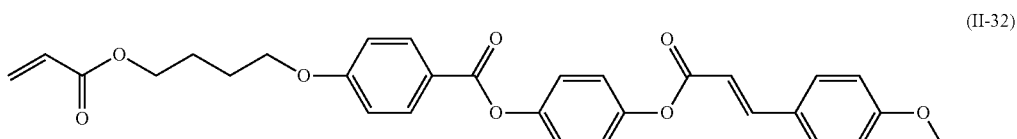
(II-33)
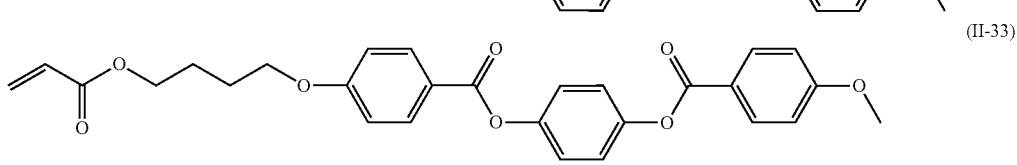
(II-34)
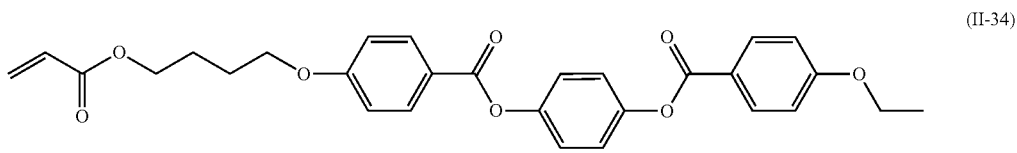
(II-35)
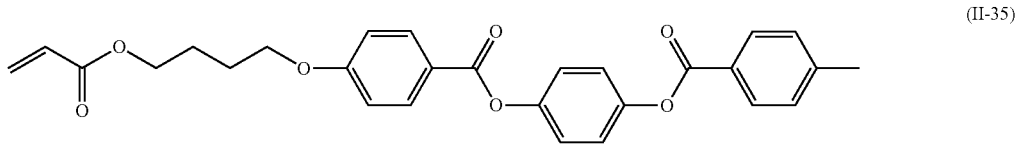

-continued
[Chemical Formula 18]
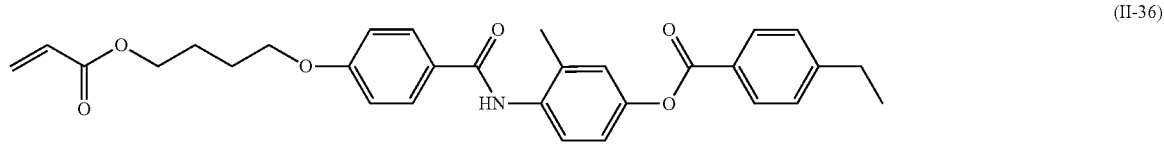
(II-36)
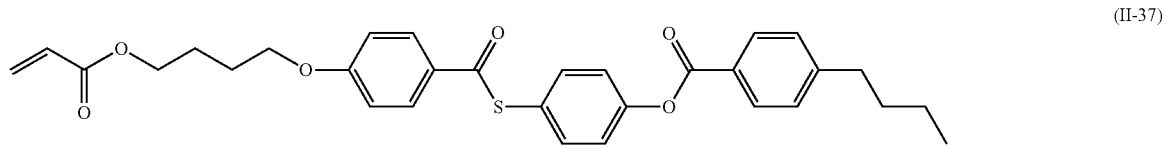
(II-37)
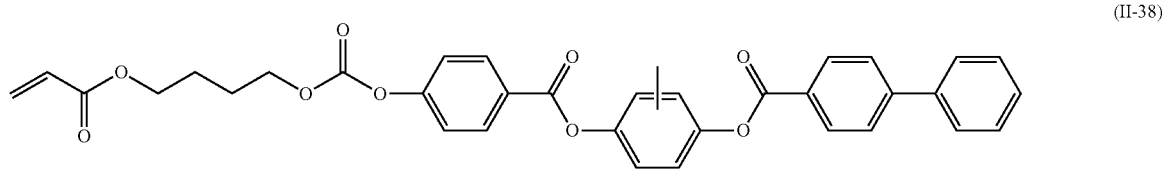
(II-38)
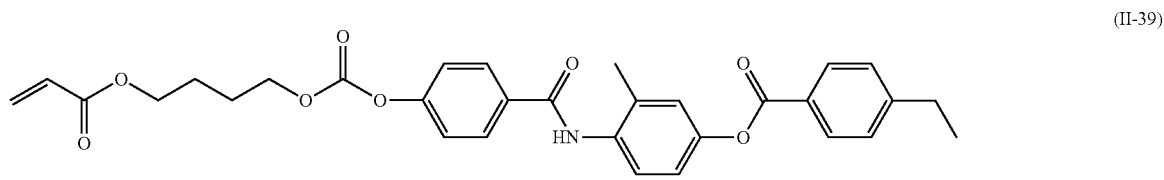
(II-39)
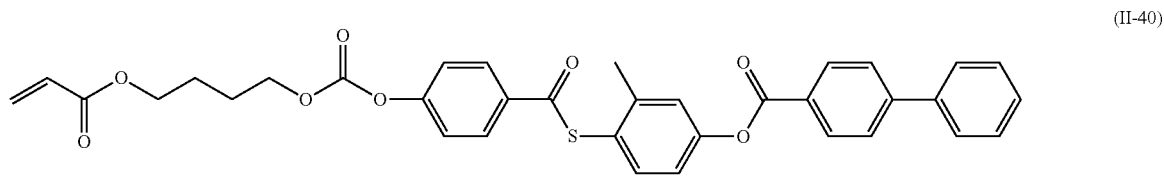
(II-40)
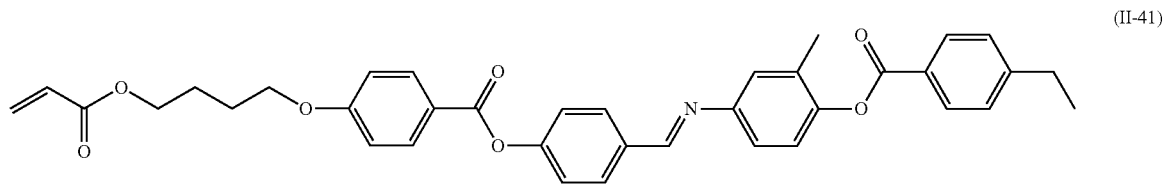
(II-41)
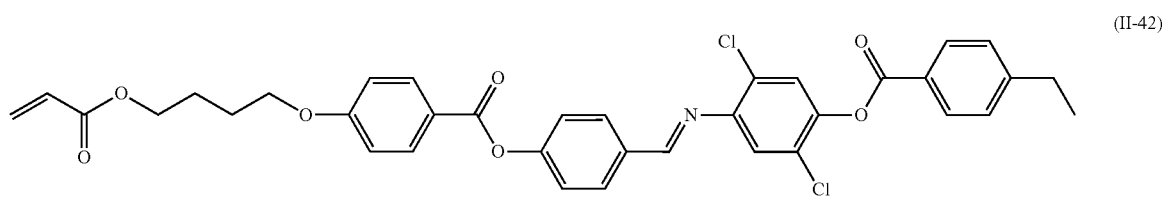
(II-42)
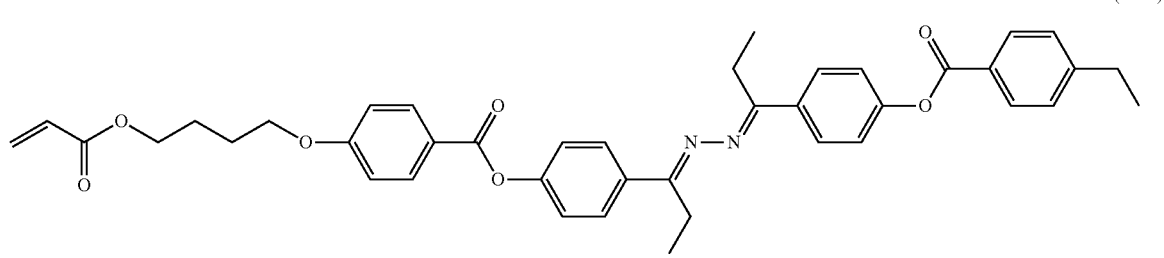
(II-43)

-continued
(II-44)
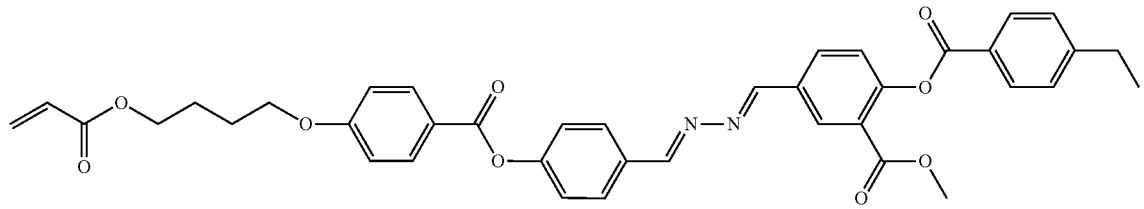
[Chemical Formula 19]
(II-45)
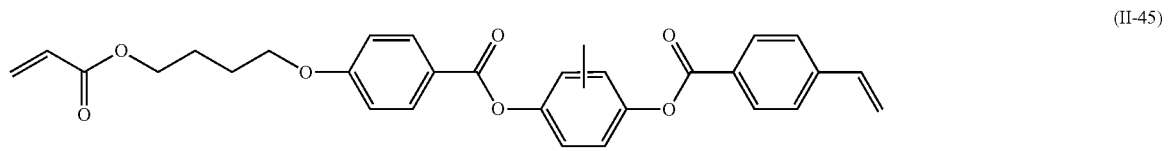
(II-46)
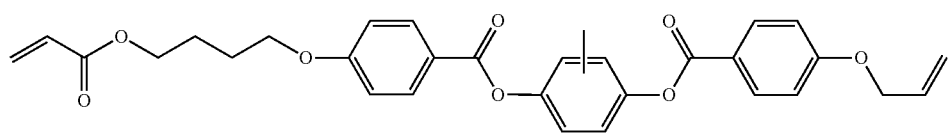
(II-47)
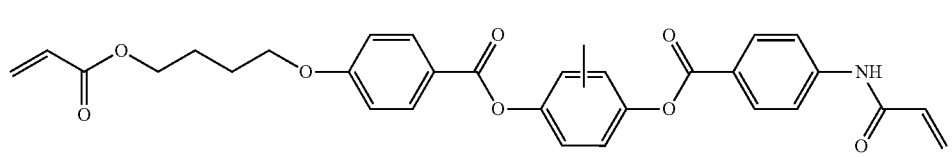
(II-48)
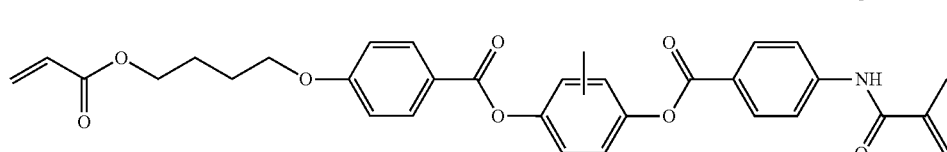
(II-49)
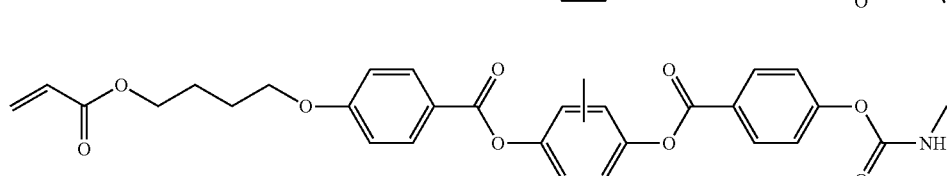
(II-50)
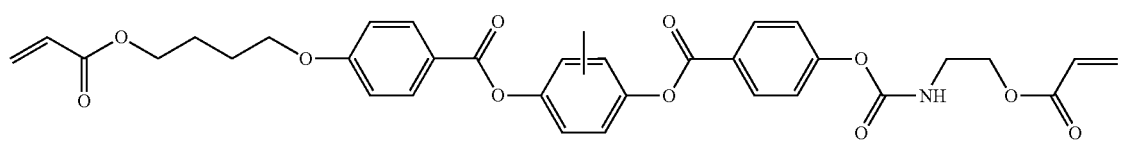
(II-51)
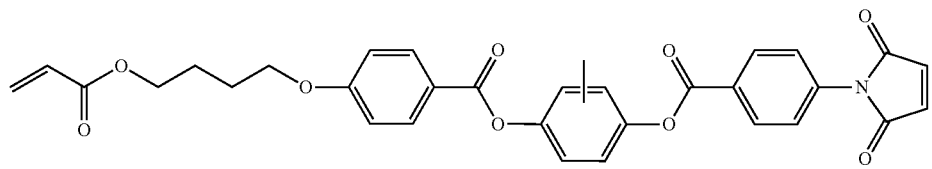
(II-52)
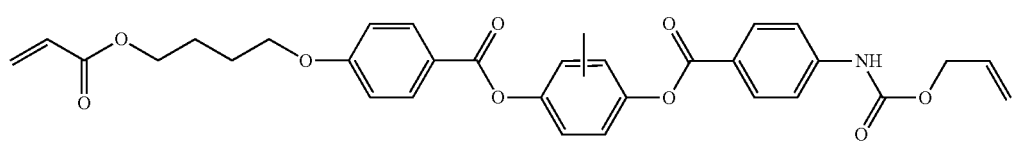

-continued
(II-53)
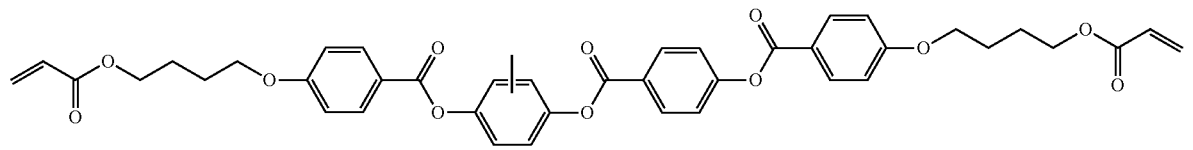
(II-54)
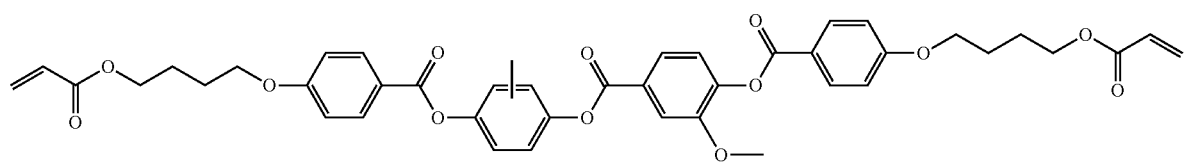
(II-55)
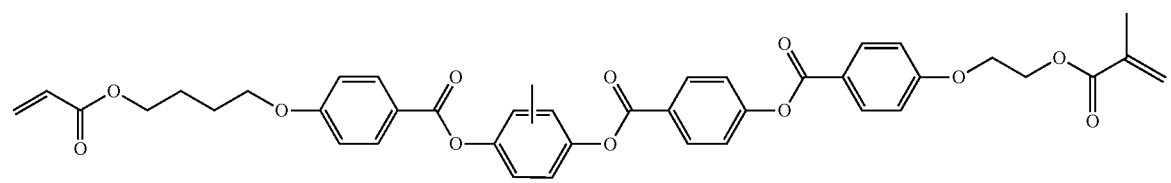
(II-56)
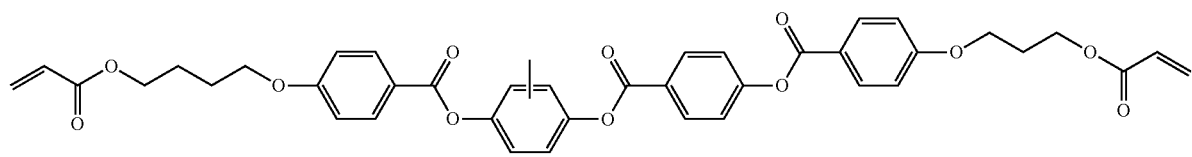
[Chemical Formula 20]
(II-57)
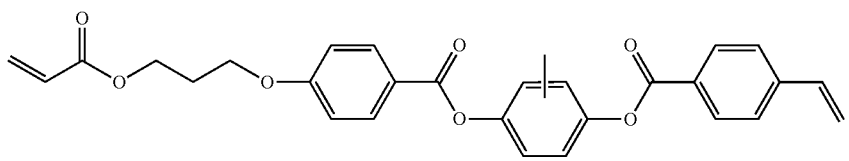
(II-58)
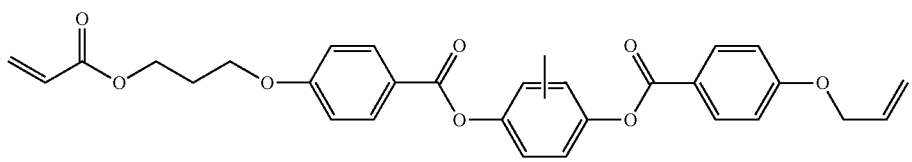
(II-59)
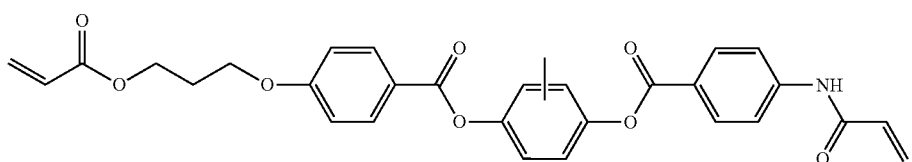
(II-60)
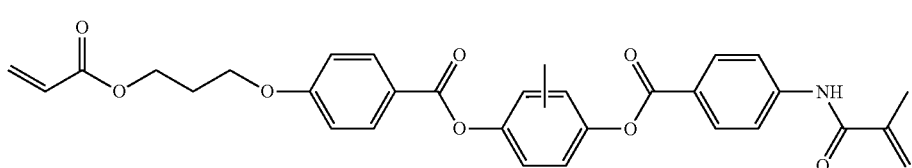
(II-61)
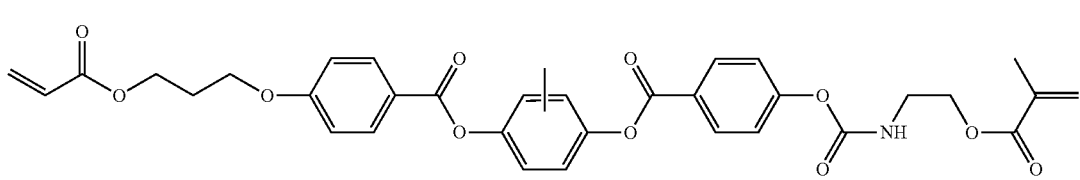

(II-62)
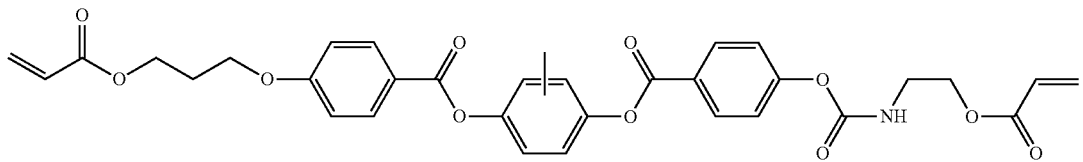
(II-63)
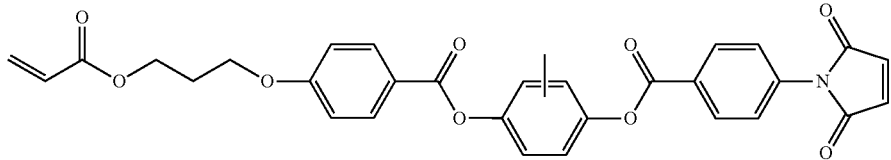
(II-64)
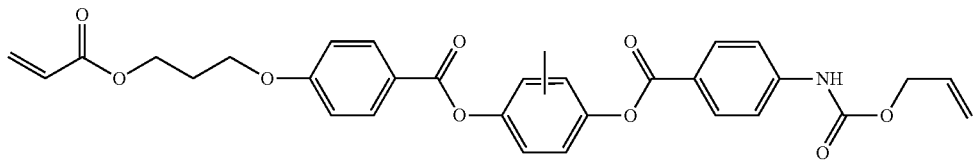
(II-65)
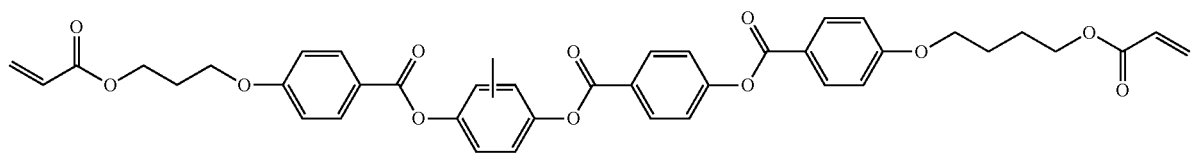
(II-66)
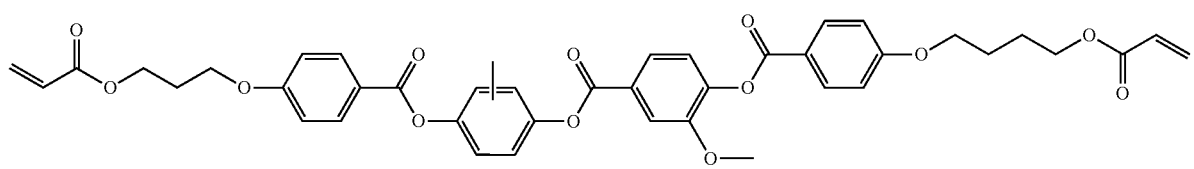
(II-67)
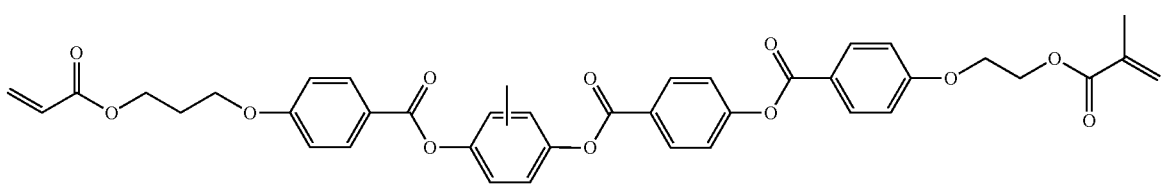
(II-68)
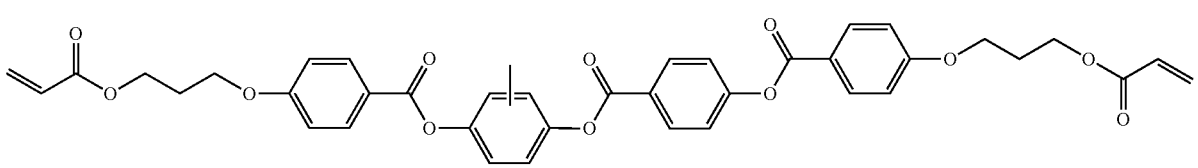
[Chemical Formula 21]
(II-69)
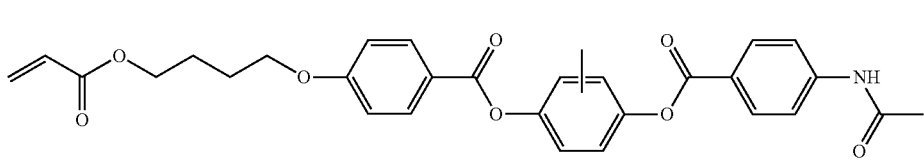
(II-70)
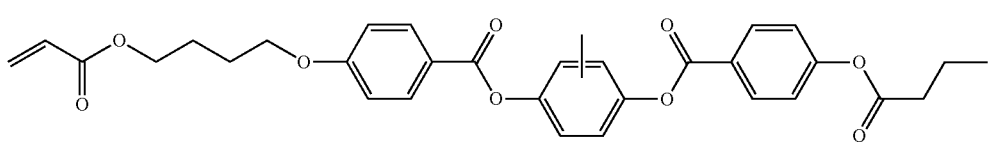

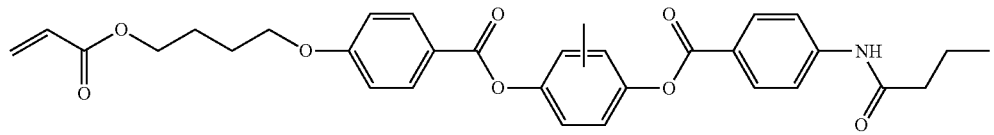
(II-71)
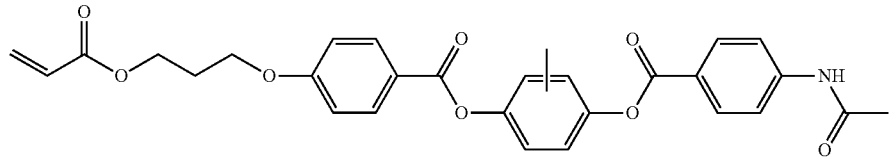
(II-72)
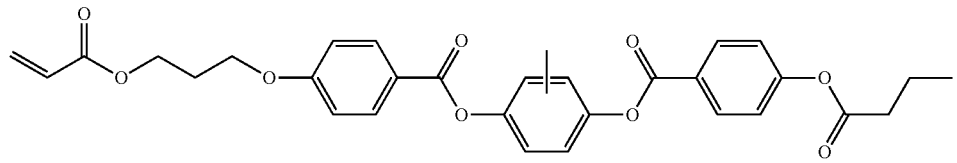
(II-73)
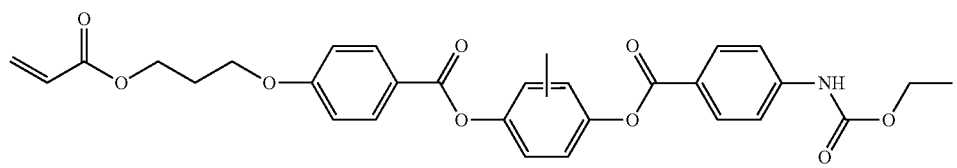
(II-74)
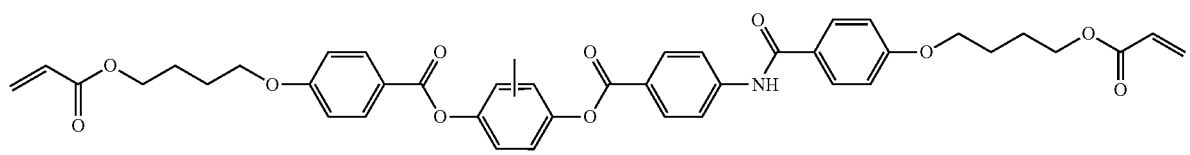
(II-75)
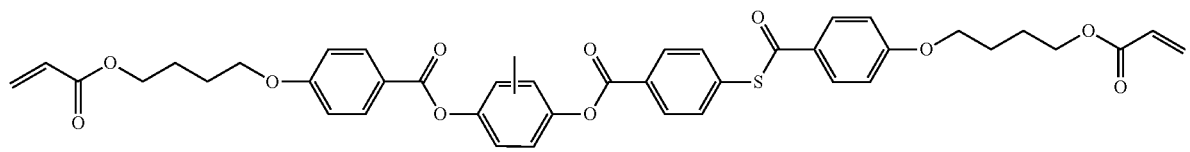
(II-76)
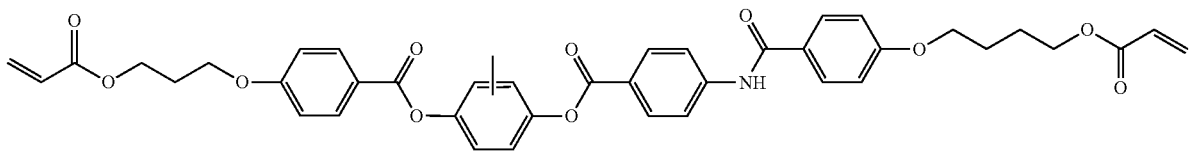
(II-77)
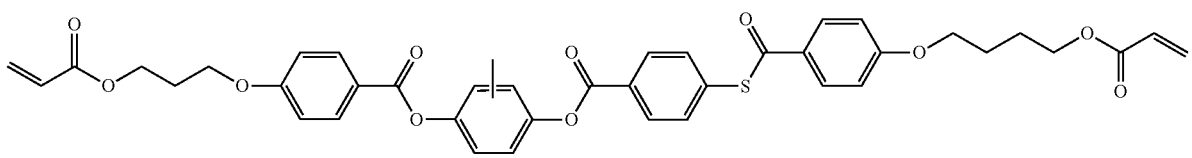
(II-78)
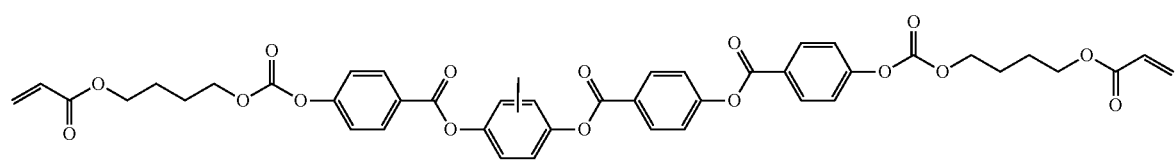
(II-79)

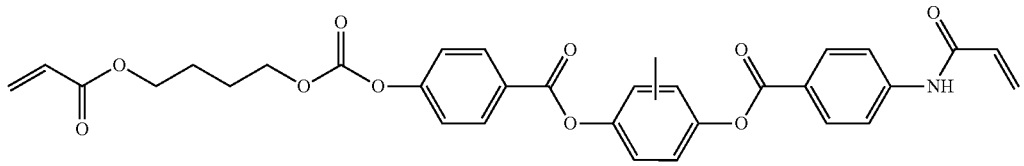
(II-80)

<Composition of Liquid Crystal Composition>

In the method for manufacturing a liquid crystal composition of the present invention, production ratio by mole of the compound represented by the formula (I) and the compound represented by the formula (II) preferably falls in the range from 50:50 to 98:2, more preferably from 60:40 to 96:4, and particularly from 70:30 to 94:6.

In the method for manufacturing a liquid crystal composition of the present invention, compositional ratio by mass of the compound represented by the formula (I) and the compound represented by the formula (II), in the liquid crystal composition, preferably falls in the range from 50:50 to 95:5, more preferably from 60:40 to 95:5, and particularly from 70:30 to 92:8.

[Liquid Crystal Composition]

The liquid crystal composition of the present invention is characterized in that it is manufactured by a method for manufacturing a liquid crystal composition of the present invention. Such liquid crystal composition has a liquid crystal structure which is different from that of a liquid crystal composition not manufactured by the method for manufacturing a liquid crystal composition of the present invention, and consequently has good solubility and crystallization suppressive performance.

The liquid crystal composition of the present invention preferably has a nematic-Iso phase transition temperature of 80 to 160° C., and more preferably 90 to 150° C.

[Film Configuration]

The film of the present invention is a film in which alignment of the liquid crystal compound in the liquid crystal composition of the present invention is fixed (for example, horizontal alignment, vertical alignment, cholesteric alignment, hybrid alignment, etc.), and shows optical anisotropy. There may be two or more optically anisotropic layers in which the alignment of the liquid crystal compound in the liquid crystal composition of the present invention is fixed. The film is usable as an optical compensation film, ½ wavelength film, ¼ wavelength film or phase difference film of liquid crystal display devices based on TN mode, IPS mode and so forth, and as a reflection filmmaking use of selective reflection ascribable to the cholesteric alignment.

(Reflection Film)

The film of the present invention is usable as a reflection film. The film of the present invention is preferably a film in which the cholesteric alignment of the liquid crystal compounds in the liquid crystal composition of the present invention is fixed.

(Other Additives)

The liquid crystal composition of the present invention when used, for example, as a reflection film making use of selective reflection ascribable to the cholesteric alignment, may contain not only the polymerizable liquid crystal, but also optionally contain solvent, compound having chiral carbon atom, polymerizable initiator (described later), and other additives (for example, cellulosic ester).

Optically Active Compound (Chiral Agent):

The liquid crystal composition may show a cholesteric liquid crystal phase, and for this purpose, preferably contains an optically active compound. Note that if the rod-like liquid crystal compound has a chiral carbon atom, it may sometimes be possible to form the cholesteric liquid crystal phase in a stable manner, without adding the optically active compound. The optically active compound is selectable from publicly known various chiral agents (for example, those described in "Ekisho Debaisu Handobukku (Handbook of Liquid Crystal Devices)", Chapter 3, Section 4-3, "TN, STN-yo Kairaru-zai (Ciral Agent for TN and STN)", p. 199, edited by the 142nd Committee of Japan Society for Promoting Science, 1989). While the optically active compound generally has a chiral carbon atom, also axially chiral compound or planar chiral compound having no chiral carbon atom is usable as the chiral agent. Examples of the axially chiral compound and the planar chiral compound include binaphthyl, helicene, paracyclophane, and derivatives of them. The optically active compound (chiral agent) may have a polymerizable group. If the optically active compound has a polymerizable group, and also the rod-like liquid crystal compound used in combination has a polymerizable group, it is now possible to form a polymer having a repeating unit derived from the rod-like liquid crystal compound and a repeating unit derived from the optically active compound, by polymerization reaction between the polymerizable optically active compound and the polymerizable rod-like liquid crystal compound. In this embodiment, the polymerizable group possessed by the polymerizable optically active compound is preferably the same species as the polymerizable group possessed by the polymerizable rod-like liquid crystal compound. Accordingly, also the polymerizable group of the optically active compound is preferably an unsaturated polymerizable group, epoxy group or aziridinyl group, more preferably an unsaturated polymerizable group, and particularly an ethylenic unsaturated polymerizable group.

The optically active compound may also be a liquid crystal compound.

The amount of consumption of the optically active compound in the liquid crystal composition is preferably 1 to 30 mol % of the liquid crystal compound used in combination. The lesser the amount of use of the optically active compound, the better since the liquid crystallinity is less likely to be adversely affected. Accordingly, the optically active compound used as the chiral agent preferably has a strong twisting power, so that a twisted alignment with a desired helical pitch may be obtained only with a small amount of consumption. Such chiral agent showing a strong twisting power is exemplified, for example, by those described in JP-A-2003-287623, which are preferably applicable to the present invention.

(Solvent)

Organic solvent is preferably used for dissolving the liquid crystal composition. Examples of the organic solvent include amides (for example, N,N-dimethylformamide), sulfoxides (for example, dimethyl sulfoxide), heterocyclic compounds (for example, pyridine), hydrocarbons (for example, benzene and hexane), alkyl halides (for example, chloroform and dichloromethane), esters (for example, methyl acetate and butyl acetate), ketones (for example, acetone, methyl ethyl ketone, cyclohexanone), and ethers (for example, tetrahydrofuran and 1,2-dimethoxyethane). Alkyl halides and ketones are preferable. Two or more organic solvents may be used in combination.

When the liquid crystal composition of the present invention is used for the optical compensation film of the liquid crystal display device, the liquid crystal composition may contain alignment controlling agent, surfactant, fluorine-containing polymer and so forth, besides the polymerization initiator (described later) and the above-described solvent.

(Alignment Controlling Agent)

Alignment controlling agent in the present invention is a compound which is typically added to a coating liquid of the liquid crystal composition of the present invention, unevenly distributes, after coated, to the surface of the layer of the liquid crystal composition, or, on the air interface side, and can therefore control alignment of the liquid crystal composition on the air interface side (air interface alignment agent). Alternatively, this is a compound which unevenly distributes, after coated, to the interface between the layer of the liquid crystal composition and the substrate, and can therefore control alignment of the liquid crystal composition on the substrate interface side, such as onium salt.

As the alignment controlling agent on the air interface side, for example, low-molecular-weight alignment controlling agent and polymer alignment controlling agent are usable. As for the low-molecular-weight alignment controlling agent, for example, paragraphs [0009] to [0083] of JP-A-2002-20363, paragraphs [0111] to [0120] of JP-A-2006-106662, and paragraphs [0021] to [0029] of JP-A-2012-211306 may be referred to, the contents of which are incorporated into the present specification. As for the polymer alignment controlling agent, for example, paragraphs [0021] to [0057] of JP-A-2004-198511, and paragraphs [0121] to [0167] of JP-A-2006-106662 may be referred to, the contents of which are incorporated into the present specification.

The amount of consumption of the alignment controlling agent is preferably 0.01 to 10% by mass of the solid content in the coating liquid containing the liquid crystal composition of the present invention, and more preferably 0.05 to 5% by mass.

By using such alignment controlling agent and alignment film, the liquid crystal compounds of the present invention may be brought into the state of homogeneous alignment, characterized by an alignment in parallel to the surface of the layer.

When the onium salt or the like is used as the alignment controlling agent on the substrate interface side, it now becomes possible to promote the homeotropic alignment, at the interface, of the liquid crystal compounds. As for the onium salt which act as a vertical alignment agent, paragraphs [0052] to [0108] of JP-A-2006-106662 may be referred to, the content of which is incorporated into the present specification.

The amount of consumption of the onium salt is preferably 0.01 to 10% by mass of the solid content in the coating liquid containing the liquid crystal composition of the present invention, and more preferably 0.5 to 5% by mass.

(Surfactant)

Surfactant is exemplified by publicly known compounds, and particularly by fluorine-containing compounds. As for the surfactant, for example, the compounds described in paragraphs [0028] to [0056] of JP-A-2001-330725, and the compounds described in paragraphs [0199] to [0207] of JP-A-2006-106662 may be referred to, the contents of which are incorporated into the present specification.

The amount of consumption of the surfactant is preferably 0.01 to 10% by mass of the solid content in the coating liquid containing the liquid crystal composition of the present invention, and more preferably 0.5 to 5% by mass.

(Other Additives Applicable to Optical Compensation Film)

As for other additives applicable to the optical compensation film, for example, the compounds described in paragraphs [0099] to [0101] of JP-A-2005-97377 may be referred to, the content of which is incorporated into the present specification.

The reflection film of the present invention may be formed, for example, by coating the liquid crystal composition of the present invention. A preferable method for forming the film of the present invention is such as coating a composition, which contains at least the liquid crystal composition of the present invention, onto the surface of the support, or onto the surface of the alignment film formed thereon, aligning the liquid crystal composition into a desired state, curing it by polymerization, and fixing the state of alignment of the liquid crystal composition.

The liquid crystal composition may be coated by any of publicly known methods (for example, extrusion coating, direct gravure coating, reverse gravure coating, die coating, bar coating, and spin coating). The liquid crystalline molecules are preferably fixed while keeping the state of alignment. The fixation is preferably carried out by a polymerization reaction involving the polymerizable group introduced into the liquid crystalline molecules.

The polymerization reaction includes thermal polymerization reaction making use of a thermal polymerization initiator, and photo-polymerization reaction making use of a photo-polymerization initiator. The photo-polymerization reaction is preferable.

Examples of the photo-polymerization initiator include α-carbonyl compounds (described in the specifications of U.S. Pat. Nos. 2,367,661 and 2,367,670), acyloin ether (described in the specification of U.S. Pat. No. 2,448,828), α-hydrocarbon-substituted aromatic acyloin compound (described in the specification of U.S. Pat. No. 2,722,512), polynuclear quinone compounds (described in the specifications of U.S. Pat. Nos. 3,046,127 and 2,951,758), combination of triarylimidazole dimer and p-aminophenyl ketone (described in the specification of U.S. Pat. No. 3,549,367), acrydine and phenazine compounds (described in the specification of JP-A-S60-105667 and U.S. Pat. No. 4,239,850), oxadiazole compound (described in the specification of U.S. Pat. No. 4,212,970), and acylphosphine oxide compounds (described in JP-B-S63-40799, JP-B-H05-29234, JP-A-H10-95788 and JP-A-H10-29997).

The amount of consumption of the photo-polymerization initiator is preferably 0.01 to 20% by mass of the solid content in the coating liquid, and more preferably 0.5 to 5% by mass. For photo-irradiation for polymerization of discotic liquid crystalline molecule, ultraviolet radiation is preferably used. Irradiation energy is preferably 20 mJ/cm$^2$ to 50 J/cm$^2$, and more preferably 100 to 800 mJ/cm$^2$. The photo-irradiation may be carried out under heating, for the purpose of accelerating the photo-polymerization reaction.

The thickness of the optically anisotropic layer composed of the liquid crystal composition is preferably 0.1 to 50 µm, and more preferably 0.5 to 30 µm.

For a particular case where selective reflectivity of the film, having the cholesteric alignment of the liquid crystal compounds fixed therein, is utilized, the thickness is more preferably 1 to 30 µm, and most preferably 2 to 20 µm. The total amount of coating of the compound represented by the formula (I) and the compound represented by the formula (II) in the liquid crystal layer (amount of coating of liquid crystal alignment accelerator) is preferably 0.1 to 500 mg/m$^2$, more preferably 0.5 to 450 mg/m$^2$, furthermore preferably 0.75 to 400 mg/m$^2$, and most preferably 1.0 to 350 mg/m$^2$.

On the other hand, when the optically anisotropic layer is used as the optical compensation film (for example, A-plate having a state of homogeneous alignment fixed therein, and C-plate having a state of homeotropic alignment fixed therein), the thickness thereof is preferably 0.1 to 50 µm, and more preferably 0.5 to 30 µm.

The alignment film may be provided by a technique such as rubbing of organic compound (preferably polymer), oblique evaporation of inorganic compound, formation of a layer having micro-grooves, or accumulation of organic compound by the Langmuir-Blodgett process (LB film) (for example, ω-tricosanoic acid, dioctadecylmethylammonium chloride, methyl stearate). Also known is an alignment film which turns to demonstrate the alignment function after exposed to electric field, magnetic field, or photo-irradiation. The alignment film formed by rubbing polymer is particularly preferable. The rubbing process is carried out by unidirectionally rubbing the surface of a polymer layer several times with paper or cloth. Species of the polymer used for the alignment film is determined depending on alignment of the liquid crystalline molecules (in particular, average tilt angle). A polymer (general polymer for forming alignment film), which is unlikely to reduce the surface energy of the alignment film is used for the purpose of horizontally aligning the liquid crystalline molecules (with an average tilt angle of 0 to 50°). A polymer capable of reducing the surface energy of the alignment film is used for the purpose of vertically aligning the liquid crystalline molecules (with an average tilt angle of 50 to 90°). In order to reduce the surface energy of the alignment film, it is preferable to introduce a $C_{10-100}$ hydrocarbon group to a side chain of the polymer.

Species of the polymer are specifically described in literatures regarding the optical compensation sheet using the liquid crystalline molecules adapted to various types of display mode.

The thickness of the alignment film is preferably 0.01 to 5 µm, and more preferably 0.05 to 1 µm. It is also possible to align, by using the alignment film, the liquid crystalline molecules for the optically anisotropic layer, and then transfer the liquid crystal layer onto a translucent support. The liquid crystalline molecules fixed in the aligned state can keep such aligned state without the alignment film. If the average tilt angle is smaller than 5°, rubbing is no longer necessary, and also the alignment film is no longer necessary. However, for the purpose of improving adhesiveness between the liquid crystalline molecules and the translucent support, it is also recommendable to use an alignment film (described in JP-A-H09-152509) which can form a chemical bond with the liquid crystalline molecule at the interface. When the alignment film is used for the purpose of improving the adhesiveness, rubbing is omissible. When two types of liquid crystal layers are provided on the same side of the translucent support, the liquid crystal layer formed on the translucent support may be allowed to function as an alignment film for the liquid crystal layer formed thereon.

The film of the present invention or an optically anisotropic element having the film of the present invention may have the translucent support. Glass plate or polymer film may be used as the translucent support, wherein the polymer film is preferably used. When stating that "the support is translucent", it means that the light transmittance is 80% or above. The translucent support generally used is an optically isotropic polymer film. The optical isotropy is preferably represented by an in-plane retardation (Re) of smaller than 10 nm, and more preferably smaller than 5 nm. As for the optically isotropic translucent support, also the thickness direction retardation (Rth) is preferably smaller than 10 nm, and more preferably smaller than 5 nm.

(Selective Reflection Characteristic)

The film of the present invention, having fixed therein the cholesteric liquid crystal phase of the liquid crystal composition of the present invention, preferably shows a selective reflection characteristic, and more preferably shows a selective reflection characteristic in the infrared wavelength region. The light reflective layer having the cholesteric liquid crystal phase fixed therein is detailed in relation to methods described in JP-A-2011-107178 and JP-A-2011-018037, which are also preferably used in the present invention.

(Laminate)

The film of the present invention is also preferably configured as a laminate of a plurality of layers each having fixed therein the cholesteric liquid crystal phase of the liquid crystal composition of the present invention. The liquid crystal composition of the present invention is also suitable for lamination, and can therefore form such laminate easily.

(Optical Compensation Film)

The film of the present invention is also usable as an optical compensation film.

When the film of the present invention is used as the optical compensation film, optical properties of the optically anisotropic layer in the optical compensation film are determined based on optical properties of a liquid crystal cell, and more specifically based on variation in the display mode. By using the liquid crystal composition of the present invention, it is now possible to manufacture the optically anisotropic layer having various optical properties adaptable to various display modes of the liquid crystal cell.

For example, as for the optically anisotropic layer for TN-mode liquid crystal cell, descriptions in JP-A-H06-214116, U.S. Pat. Nos. 5,583,679, 5,646,703 and German Patent No. 3911620A1 may be referred to, the contents of which are incorporated into the present specification. As for the optically anisotropic layer for IPS-mode or FLC-mode liquid crystal cell, descriptions in JP-A-H09-292522 and JP-A-H10-54982 may be referred to, the contents of which are incorporated into the present specification. As for the optically anisotropic layer for OCB-mode or HAN-mode liquid crystal cell, the descriptions in U.S. Pat. No. 5,805,253 and International Patent Application WO96/37804 may be referred to, the contents of which are incorporated into the present specification. As for the optically anisotropic layer for STN-mode liquid crystal cell, the description in JP-A-H09-26572 may be referred to, the content of which is incorporated into the present specification. As for the optically anisotropic layer for VA-mode liquid crystal cell, the description in Japanese Patent JP-1302-2866372 may be referred to, the content of which is incorporated into the present specification.

In particular, in the present invention, the film of this invention is preferably used as the optically anisotropic layer of the IPS-mode liquid crystal cell.

For example, a film having an optically anisotropic layer, in which the liquid crystal compounds of the present invention is in the state of homogeneous alignment, is usable as an A-plate. The A-plate now means a uniaxial birefringent layer characterized by the refractive index in the slow axis direction larger than the refractive index in the thickness direction. When the film of the present invention is the A-plate, only a single optically anisotropic layer will suffice for compensation, if the layer shows an in-plane retardation (Re) of 200 nm to 350 nm at 550 nm.

A film having an optically anisotropic layer, in which the liquid crystal compounds of the present invention is in the state of homeotropic alignment, is usable as a positive C-plate, possibly in combination with a biaxial film or the like. The positive C-plate now means a uniaxial birefringent layer characterized by the refractive index in the thickness direction larger than the in-plane refractive index. The film of the present invention, used as the positive C-plate, preferably has an in-plane retardation (Re) at 550 nm of −10 nm to 10 nm, and a thickness direction retardation (Rth) at 550 nm of −250 to −50 nm, although depending on optical characteristics of the biaxial film to be combined.

[Polarizing Plate]

The present invention also relates to a polarizing plate having at least the film with the optically anisotropic layer (optical compensation film), and a polarizing film. In the polarizing plate having a polarizing film and a protective film disposed at least on one side thereof, the optically anisotropic layer is usable as such protective film.

Alternatively, in the polarizing plate configured to have the protective films on both sides of the polarizing film, the optically anisotropic layer is also usable as one of these protective films.

The polarizing film includes iodine-containing polarizing film, dye-containing polarizing film using dichroic dye, and polyene-based polarizing film. The iodine-containing polarizing film and the dye-containing polarizing film may be manufactured generally by using polyvinyl alcohol-based film.

Although the thickness of the polarizing film is not specifically limited, the thinner the polarizing film, the more thinner will be the polarizing plate and liquid crystal display device into which it is incorporated. From this point of view, the thickness of the polarizing film is preferably 10 µm or smaller. Since the optical path length in the polarizing film is necessarily longer than the wavelength of light, so that the minimum thickness of the polarizing film is preferably 0.7 µm or larger, substantially 1 µm or larger, and generally 3 µm or larger.

[Liquid Crystal Display Device]

The present invention also relates to a liquid crystal display device having such polarizing plate. The liquid crystal display device may have any alignment mode, without special limitation, such as TN mode, IPS mode, FLC mode, OCB mode, HAN mode, or VA mode. As for the liquid crystal display device making use of VA mode, the description in paragraphs [0109] to [0129] of JP-A-2005-128503 may be referred to, the content of which is incorporated into the present specification. As for the liquid crystal display device making use of IPS mode, the description in paragraphs [0027] to [0050] of JP-A-2006-106662 may be referred to, the content of which is incorporated into the present specification.

For the liquid crystal display device of the present invention, for example, the A-plate and C-plate described above are usable.

The optically anisotropic layer may be incorporated into the liquid crystal display device, in the form of polarizing plate obtained by bonding with the polarizing film. Alternatively, the optically anisotropic layer may be incorporated as a viewing angle compensation film which is configured by the optically anisotropic layer by itself, or by a laminate combined with other phase difference layer. The other phase difference layer to be combined is selectable, depending on the alignment mode of the liquid crystal cell in need of compensation of viewing angle.

The optically anisotropic layer may be disposed between the liquid crystal cell and the polarizing film on the viewer's side, or between the liquid crystal cell and the polarizing film on the back light side.

In this description, Re(Λ) and Rth (Λ) are retardation (nm) in plane and retardation (nm) along the thickness direction, respectively, at a wavelength of Λ. Re(Λ) is measured by applying light having a wavelength of Λ nm to a film in the normal direction of the film, using KOBRA 21ADH or WR (by Oji Scientific Instruments). The selection of the measurement wavelength may be conducted according to the manual-exchange of the wavelength-selective-filter or according to the exchange of the measurement value by the program.

When a film to be analyzed is expressed by a monoaxial or biaxial index ellipsoid, Rth (Λ) of the film is calculated as follows.

Rth (Λ) is calculated by KOBRA 21ADH or WR on the basis of the six Re(Λ) values which are measured for incoming light of a wavelength Λ nm in six directions which are decided by a 100 step rotation from 0° to 50° with respect to the normal direction of a sample film using an in-plane slow axis, which is decided by KOBRA 21ADH, as an inclination axis (a rotation axis; defined in an arbitrary in-plane direction if the film has no slow axis in plane), a value of hypothetical mean refractive index, and a value entered as a thickness value of the film.

In the above, when the film to be analyzed has a direction in which the retardation value is zero at a certain inclination angle, around the in-plane slow axis from the normal direction as the rotation axis, then the retardation value at the inclination angle larger than the inclination angle to give a zero retardation is changed to negative data, and then the Rth (Λ) of the film is calculated by KOBRA 21ADH or WR.

Around the slow axis as the inclination angle (rotation angle) of the film (when the film does not have a slow axis, then its rotation axis may be in any in-plane direction of the film), the retardation values are measured in any desired inclined two directions, and based on the data, and the estimated value of the mean refractive index and the inputted film thickness value, Rth may be calculated according to formulae (1) and (2):

[Mathematical 1]

$$Re(\theta) = \left[ nx - \frac{ny \times nz}{\sqrt{\left\{ ny\sin\left(\sin^{-1}\left(\frac{\sin(-\theta)}{nx}\right)\right)\right\}^2 + \left\{ nz\cos\left(\sin^{-1}\left(\frac{\sin(-\theta)}{nx}\right)\right)\right\}^2}} \right] \times \frac{d}{\cos\left\{\sin^{-1}\left(\frac{\sin(-\theta)}{nx}\right)\right\}} \quad \text{formulae (1)}$$

$$Rth = \{(nx + ny)/2 - nz\} \times d \quad \text{formulae (2)}$$

Re(Θ) represents a retardation value in the direction inclined by an angle Θ from the normal direction; nx represents a refractive index in the in-plane slow axis direction; ny represents a refractive index in the in-plane direction perpendicular to nx; and nz represents a refractive index in the direction perpendicular to nx and ny. And "d" is a thickness of the film.

When the film to be analyzed is not expressed by a monoaxial or biaxial index ellipsoid, or that is, when the film does not have an optical axis, then Rth(Λ) of the film may be calculated as follows:

Re(Λ) of the film is measured around the slow axis (judged by KOBRA 21ADH or WR) as the in-plane inclination axis (rotation axis), relative to the normal direction of the film from −50° up to +50° at intervals of 10°, in 11 points in all with a light having a wavelength of Λnm applied in the inclined direction; and based on the thus-measured retardation values, the estimated value of the mean refractive index and the inputted film thickness value, Rth(Λ) of the film may be calculated by KOBRA 21ADH or WR.

In the above-described measurement, the hypothetical value of mean refractive index is available from values listed in catalogues of various optical films in Polymer Handbook (John Wiley & Sons, Inc.). Those having the mean refractive indices unknown can be measured using an Abbe refract meter. Mean refractive indices of some main optical films are listed below:

cellulose acylate (1.48), cycloolefin polymer (1.52), polycarbonate (1.59), polymethylmethacrylate (1.49) and polystyrene (1.59). KOBRA 21ADH or WR calculates nx, ny and nz, upon enter of the hypothetical values of these mean refractive indices and the film thickness. On the basis of thus-calculated nx, ny and nz, Nz=(nx−nz)/(nx−ny) is further calculated.

In this specification, the wavelength at which the refraction index is measured is 550 nm unless otherwise specified.

EXAMPLES

Paragraphs below will further specifically describe features of the present invention, referring to Examples and Comparative Examples. Any materials, amount of use, ratio, details of processing, procedures of processing and so forth shown in Examples may appropriately be modified without departing from the spirit of the present invention. Therefore, it is to be understood that the scope of the present invention should not be interpreted in a limited manner based on the specific examples shown below Example 1

Compound (IV-1) (21 g, 80 mmol) and Compound (V-1) (1.3 g, 8.9 mmol) were mixed with ethyl acetate (24 mL), tetrahydrofuran (22 mL) and triethylamine (13 mL). The obtained solution was slowly added dropwise to an ethyl acetate solution of methanesulfonyl chloride (10 g, 89 mmol) under cooling on ice. Feed ratio by mole of Compound (IV-1) and Compound (V-1) was 90:10.

Next, the mixture was stirred for one hour under cooling on ice, an ethyl acetate solution of Compound (III-1) was added dropwise under cooling on ice, and then triethylamine (14 mL) was slowly added dropwise under cooling on ice.

The mixture was then stirred for two hours while keeping the reaction temperature at 20° C., water (60 g) was added for extraction into an organic layer, and the organic layer was washed with a 2% aqueous hydrochloric acid solution and a 10% brine in this order.

A portion of the organic layer was sampled and subjected to HPLC analysis, and production ratio of Compound (I-1) and Compound (II-1) was estimated based on the ratio of peak areas. The production ratio by mole was found to be 82:18. The obtained result was listed in Table 1 below.

Next, the organic layer was filtered under suction, methanol/water was added to the filtrate so as to allow crystal to deposit, and the resultant crystal was collected by filtration, to thereby obtain a liquid crystal composition containing Compound (I-1) and Compound (II-1) (yield=21.6 g).

The obtained liquid crystal composition was sampled and subjected to HPLC analysis, and compositional ratio of Compound (I-1) and Compound (II-1) was estimated based on the ratio of peak areas. The compositional ratio by mass was found to be 89:11. The obtained result was listed in Table 1 below.

The liquid crystal composition was found to show a nematic-Iso phase transition temperature of 115° C.

Note that the production ratio and the compositional ratio of Compound (I-1) and Compound (II-1) were estimated using standard curves determined based on the ratio of peak areas in HPLC analyses, using standard samples of separately synthesized Compound (I-1) and Compound (II-1).

Examples 2 to 13

Synthesis of liquid crystal compositions containing the compound represented by the formula (I) and the compound represented by the formula (II), measurement of the production ratio of the compound represented by the formula (I) and the compound represented by the formula (II) in the obtained liquid crystal composition, and measurement of the compositional ratio of the compound represented by the formula (I) and the compound represented by the formula (II) in the obtained liquid crystal composition, were carried out according to the same experimental procedures as in Example 1, except that species of the compound represented by the formula (III), the compound represented by the formula (IV) and the compound represented by the formula (V); and the feed ratio of the compound represented by the formula (IV) and the compound represented by the formula (V), were altered.

The obtained results were listed in Table 1 below.

TABLE 1

| | Kind of raw material of compound | | | Feed ratio of the carboxylic acid (molar ratio) | | Type of the resulting compound | | Production ratio of compound (I) and (II) (molar ratio) | | Composition ratio of the liquid crystal composition (weight ratio) | |
|---|---|---|---|---|---|---|---|---|---|---|---|
| | compound (III) | compound (IV) | compound (V) | compound (IV) | compound (V) | compound (I) | compound (II) | compound (I) | compound (II) | compound (I) | compound (II) |
| Example 1 | III-1 | IV-1 | V-1 | 90 | 10 | I-1 | II-1 | 82 | 18 | 89 | 11 |
| Example 2 | III-1 | IV-1 | V-1 | 80 | 20 | I-1 | II-1 | 71 | 29 | 78 | 22 |

TABLE 1-continued

| | Kind of raw material of compound | | | Feed ratio of the carboxylic acid (molar ratio) | | Type of the resulting compound | | Production ratio of compound (I) and (II) (molar ratio) | | Composition ratio of the liquid crystal composition (weight ratio) | |
|---|---|---|---|---|---|---|---|---|---|---|---|
| | compound (III) | compound (IV) | compound (V) | compound (IV) | compound (V) | compound (I) | compound (II) | compound (I) | compound (II) | compound (I) | compound (II) |
| Example 3 | III-1 | IV-1 | V-2 | 90 | 10 | I-1 | II-2 | 80 | 20 | 87 | 13 |
| Example 4 | III-1 | IV-1 | V-4 | 80 | 20 | I-1 | II-4 | 68 | 32 | 70 | 30 |
| Example 5 | III-1 | IV-1 | V-4 | 88 | 12 | I-1 | II-4 | 82 | 18 | 83 | 17 |
| Example 6 | III-1 | IV-1 | V-4 | 90 | 10 | I-1 | II-4 | 84 | 16 | 86 | 14 |
| Example 7 | III-1 | IV-1 | V-4 | 92 | 8 | I-1 | II-7 | 89 | 11 | 91 | 9 |
| Example 8 | III-1 | IV-1 | V-5 | 90 | 10 | I-1 | II-5 | 84 | 16 | 87 | 13 |
| Example 9 | III-1 | IV-1 | V-7 | 80 | 20 | I-1 | II-7 | 66 | 34 | 76 | 24 |
| Example 10 | III-1 | IV-1 | V-7 | 90 | 10 | I-1 | II-7 | 82 | 18 | 86 | 14 |
| Example 11 | III-1 | IV-1 | V-9 | 90 | 10 | I-1 | II-9 | 81 | 19 | 87 | 13 |
| Example 12 | III-6 | IV-1 | V-1 | 90 | 10 | I-9 | II-27 | 80 | 20 | 93 | 7 |
| Example 13 | III-1 | IV-3 | V-1 | 90 | 10 | I-1 | II-8 | 82 | 18 | 88 | 12 |

Example 84

Synthesis of Carboxylic Acid (V-29)

Hydroquinone monomethyl ether (37 mg) was added to a tetrahydrofuran (THF) solution (17 mL) of methanesulfonyl chloride (33.0 mmol, 2.6 mL), and the inner temperature was cooled down to −5° C. To the solution, a THF solution (16 mL) of Compound (IV-1) (31.5 mmol, 8.33 g) and diisopropylethylamine (33.0 mmol, 5.75 mL) was added dropwise, so as not to elevate the inner temperature to or above 0° C. The mixture was stirred at −5° C. for 30 minutes, and diisopropylethylamine (33.0 mmol, 5.75 mL), a THF solution (20 mL) of p-hydroxybenzaldehyde, and 4-dimethylaminopyridine (DMAP) (one spatula) were added. The mixture was then stirred at room temperature for four hours. To the mixture, added was methanol (5 mL) to terminate the reaction, and further added were water and ethyl acetate. An organic layer as a result of extraction with ethyl acetate was evaporated using a rotary evaporator to remove the solvent, the residue was dissolved in acetonitrile (67 mL), then added were an aqueous solution (2 mL) of sodium hypochlorite (42.0 mmol, 3.80 g), an aqueous solution (8.2 mL) of sodium dihydrogen phosphate dihydrate (6.0 mmol, 0.94 g), and hydrogen peroxide solution (4.0 mL), and the mixture was stirred at room temperature for 12 hours. One hundred milliliters of a 1 N aqueous hydrochloric acid solution was added thereto, and the solution was filtered. The residue was washed with a small amount of acetonitrile, to obtain carboxylic acid (V-29). The carboxylic acid (V-29) is Exemplary Compound (V-29) of the compound represented by the formula (V) above.

Synthesis of Liquid Crystal Composition

Compound (IV-1) (54 g, 204 mmol) and Compound (V-29) (6.8 g, 17.7 mmol) were mixed with ethyl acetate (50 mL), THF (45 mL) and diisopropylethylamine (41.8 mL). The obtained solution was added dropwise to an ethyl acetate solution of methanesulfonyl chloride (25.5 g, 223 mmol), slowly under cooling on ice. The feed ratio by mole of Compound (IV-1) and Compound (V-1) was 92:8.

Next, the mixture was stirred for one hour under cooling on ice, an ethyl acetate solution of Compound (III-1) (13.5 g, 109 mmol) was added dropwise under cooling on ice, N-methylimidazole (0.5 g) was further added, and thereto triethylamine (33.7 mL) was slowly added dropwise under cooling on ice.

The mixture was then stirred for two hours while keeping the reaction temperature at 20° C., water (140 mL) was added for extraction into an organic layer, and the organic layer was washed with a 2% aqueous hydrochloric acid solution and a 10% brine in this order.

A portion of the organic layer was sampled and subjected to HPLC analysis, and production ratio of Compound (I-1) and Compound (II-53) was estimated based on the ratio of peak areas. The production ratio by mole was found to be 88:12. The obtained result was listed in Table 2 below.

Next, the organic layer was filtered under suction, methanol/water was added to the filtrate so as to allow crystal to deposit, and the resultant crystal was collected by filtration, to thereby obtain a liquid crystal composition containing Compound (I-1) and Compound (II-53) (yield=60 g).

The obtained liquid crystal composition was sampled and subjected to HPLC analysis, and compositional ratio of Compound (I-1) and Compound (II-53) was estimated based on the ratio of peak areas. The compositional ratio by mass was found to be 87:113. The obtained result was listed in Table 2 below.

The liquid crystal composition was found to show a nematic-Iso phase transition temperature of 140° C.

Note that the production ratio and the compositional ratio of Compound (I-1) and Compound (II-53) were estimated using standard curves determined based on the ratio of peak areas in HPLC analyses, using standard samples of separately synthesized Compound (I-1) and Compound (II-53).

Synthesis of liquid crystal compositions containing the compound represented by the formula (I) and the compound represented by the formula (II), measurement of the production ratio of the compound represented by the formula (I) and the compound represented by the formula (II) in the obtained liquid crystal composition, and measurement of the compositional ratio of the compound represented by the formula (I) and the compound represented by the formula (II) in the obtained liquid crystal composition, were carried out according to the same experimental procedures as in Example 84, except that species of the compound represented by the formula (III), the compound represented by the formula (IV) and the compound represented by the formula (V); and the feed ratio of the compound represented by the formula (IV) and the compound represented by the formula (V), were altered.

The obtained results were listed in Table 2 below.

TABLE 2

| | Kind of raw material of compound | | | Feed ratio of the carboxylic acid (molar ratio) | | Type of the resulting compound | | Production ratio of compound (I) and (II) (molar ratio) | | Composition ratio of the liquid crystal composition (weight ratio) | |
|---|---|---|---|---|---|---|---|---|---|---|---|
| | compound (III) | compound (IV) | compound (V) | compound (IV) | compound (V) | compound (I) | compound (II) | compound (I) | compound (II) | compound (I) | compound (II) |
| Example 84 | III-1 | IV-1 | V-29 | 92 | 8  | I-1 | II-53 | 88 | 12 | 87 | 13 |
| Example 85 | III-1 | IV-1 | V-20 | 90 | 10 | I-1 | II-45 | 87 | 13 | 90 | 10 |
| Example 86 | III-1 | IV-1 | V-21 | 90 | 10 | I-1 | II-46 | 80 | 19 | 82 | 18 |
| Example 87 | III-1 | IV-1 | V-25 | 90 | 10 | I-1 | II-47 | 85 | 15 | 90 | 10 |
| Example 88 | III-1 | IV-1 | V-26 | 90 | 10 | I-1 | II-48 | 85 | 15 | 88 | 12 |
| Example 89 | III-1 | IV-1 | V-23 | 90 | 10 | I-1 | II-49 | 86 | 14 | 86 | 14 |
| Example 90 | III-1 | IV-1 | V-28 | 90 | 10 | I-1 | II-52 | 84 | 16 | 85 | 15 |
| Example 91 | III-1 | IV-1 | V-30 | 92 | 8  | I-1 | II-54 | 88 | 12 | 88 | 12 |
| Example 92 | III-1 | IV-1 | V-31 | 91 | 9  | I-1 | II-55 | 86 | 14 | 84 | 16 |
| Example 93 | III-1 | IV-1 | V-32 | 91 | 9  | I-1 | II-56 | 86 | 14 | 84 | 16 |
| Example 94 | III-1 | IV-3 | V-25 | 90 | 10 | I-3 | II-59 | 84 | 16 | 89 | 11 |
| Example 95 | III-1 | IV-3 | V-32 | 92 | 8  | I-3 | II-68 | 88 | 12 | 87 | 13 |

Comparative Example 1

Compound (II-1) was synthesized according to the scheme below.

[Chemical Formula 22]

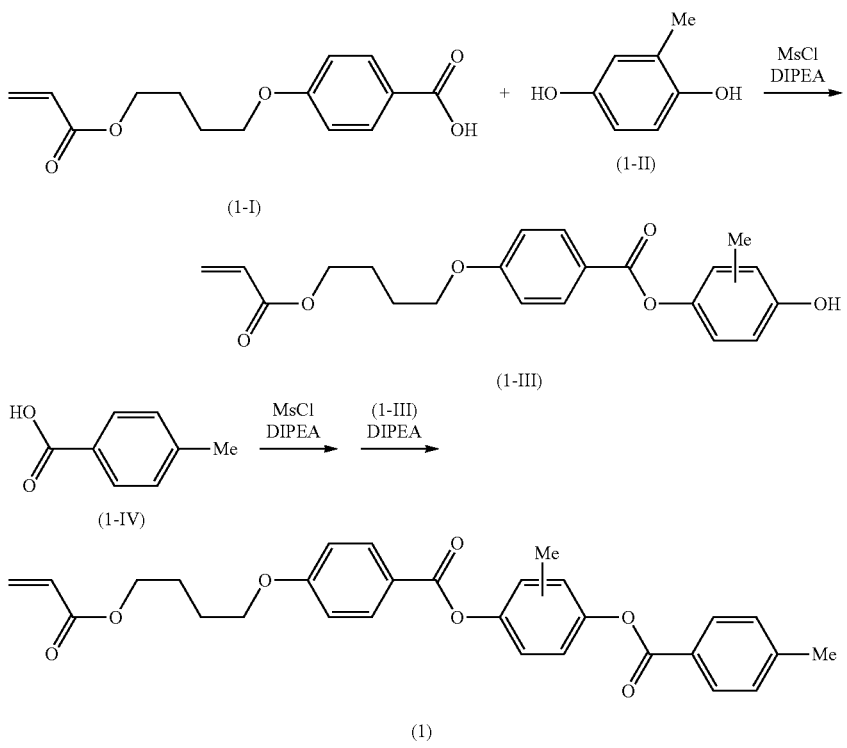

BHT (37 mg) was added to a tetrahydrofuran (THF) solution (20 mL) containing methanesulfonyl chloride (10.22 g), and the inner temperature was cooled down to −5° C. To the mixture, a THF solution (50 mL) containing Compound (IV-1) (31.5 mmol, 8.33 g) and diisopropylethylamine (17.6 mL) was added dropwise, so as not to elevate the inner temperature to 0° C. or above. The mixture was stirred at −5° C. for 30 minutes, and thereto diisopropylethylamine (16.7 mL) and a THF solution (20 mL) containing Compound (III-1), and DMAP (one spatula) were added. The mixture was then stirred at room temperature for four hours. To the mixture added was methanol (5 mL) to terminate the reaction, and further added were water and ethyl acetate. An organic layer as a result of extraction with ethyl acetate was evaporated using a rotary evaporator to remove the solvent, and the residue was purified by silica gel column chromatography, to obtain Compound (VI-1).

BHT (3 mg) was added to a tetrahydrofuran (THF) solution (10 mL) containing methanesulfonyl chloride (3.5 g), and the inner temperature was cooled down to −5° C. To the mixture, a THF solution (20 mL) containing Compound (V-1) (4.4 g) and diisopropylethylamine (4.7 mL) was added dropwise, so as not to elevate the inner temperature to 0° C. or above. The mixture was stirred at −5° C. for 30 minutes, and thereto diisopropylethylamine (4.7 mL) and a THF solution (20 mL) containing Compound (VI-1), and DMAP (one spatula) were added. The mixture was then stirred at room temperature for two hours. To the mixture added was methanol (50 mL) to terminate the reaction, and further added were water and ethyl acetate. An organic layer as a result of extraction with ethyl acetate was evaporated using a rotary evaporator to remove the solvent, to obtain a crude product of Compound (II-1). Purification by silica gel column chromatography gave Compound (II-1) in a yield of 59%.

Mixed were 8.9 g of Compound (I-1), 1.1 g of Compound (II-1), and 20 g of methyl ethyl ketone at 25° C., and the obtained liquid crystal composition was denoted as a liquid crystal composition of Comparative Example 1.

Comparative Example 2

Compound (II-4) was obtained according to the synthetic method same as the method for synthesizing Compound (II-1) in Comparative Example 1, except that Compound (V-4) was used in place of Compound (I-1).

Mixed were 8.6 g of Compound (I-1), 1.4 g of Compound (II-4), and 20 g of methyl ethyl ketone at 25° C., and the obtained liquid crystal composition was denoted as a liquid crystal composition of Comparative Example 2.
<Solubility Test>
(Solubility Test 1)

Ten grams of the liquid crystal composition manufactured in Example 1 and 20 g of methyl ethyl ketone were mixed at 25° C. The entire solid completely dissolved within two minutes, proving a good solubility.

On the other hand, the solution containing the liquid crystal composition of Comparative Example 1 was visually found to contain a slight amount of undissolved solid, two minutes after the preparation. It was, however, confirmed that the entire portion completely dissolved after five minutes.
(Solubility Test 2)

Ten grams of the liquid crystal composition synthesized in Example 6 and 20 g of methyl ethyl ketone were added at 25° C. The solid was completely dissolved within five minutes, proving a good solubility.

On the other hand, the solution containing the liquid crystal composition of Comparative Example 2 was visually found to contain a slight amount of undissolved solid, five minutes after the preparation.
(Other Solubility Tests)

Solubility test was carried out also using the other liquid crystal compositions manufactured in Examples 2 to 5 and 7 to 12 in the same way, proving that the solubility was improved.
<Powder X-Ray Diffractometry>
(X-Ray Diffractometry 1)

The liquid crystal composition obtained in Example 1, and a solid obtained by thoroughly mixing two species of liquid crystal compounds used in Comparative Example 1, were respectively analyzed by powder X-ray diffractometry using RINT2000 from Rigaku Corporation, in a measurement range of $2\Theta=5°$ to $55°$, using the CuKα line as an incident X-ray.

As illustrated in FIG. 1, an X-ray diffraction spectrum of the liquid crystalline composition of Example 1 was different from an X-ray diffraction spectrum of the liquid crystalline composition of Comparative Example 1.

From the results of the test, it was found that the liquid crystal composition obtained in Example 1 was different in crystal structure different from the solid mixture of two liquid crystal compounds used in Comparative Example 1.
(X-Ray Diffractometry 2)

The liquid crystal composition obtained in Example 6, and a solid obtained by thoroughly mixing two species of liquid crystal compounds used in Comparative Example 2, were respectively analyzed by powder X-ray diffractometry in the same way as in X-Ray Diffractometry 1.

Figure 2:
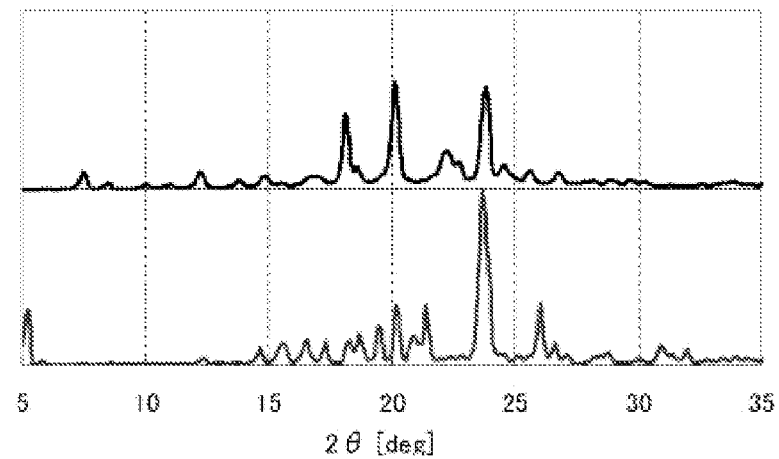
FIG. 2 An X-ray diffraction spectral chart of a liquid crystalline composition of Example 6 and a liquid crystalline composition of Comparative Example 2.

As illustrated in FIG. 2, an X-ray diffraction spectrum of the liquid crystalline composition of Example 6 was different from an X-ray diffraction spectrum of the liquid crystalline composition of Comparative Example 2.

From the results of the test, it was found that the liquid crystal composition obtained in Example 6 was different in crystal structure from the solid mixture of two liquid crystal compounds used in Comparative Example 2.

Example 16

<Preparation of Polymerizable Composition>

Coating liquid (A) of a liquid crystalline composition, having the compositional ratio below, was prepared using the composition of Example 1:

| Composition of Example 1 | 100 parts by mass |
| MEK | 233 parts by mass |

<Preparation of Coated Sample>

Next, using the thus obtained liquid crystalline composition, a film of Example 16 was manufactured.

On a cleaned glass substrate, polyimide alignment film SE-130 from Nissan Chemical Industries, Ltd. was formed by spin coating, dried, and baked at 250° C. for one hour. The obtained film was rubbed to thereby manufacture a substrate with alignment film. On the rubbed surface of the alignment film of the substrate, coating liquid (A) of liquid crystalline composition was coated at room temperature by spin coating, and the coating was allowed to stand at room temperature for 30 minutes.
(Evaluation of Suppressive Effect on Crystal Deposition)

An arbitrary region of the surface of the liquid crystal film, in the thus obtained coated film of Example 16, was visually observed under a polarizing microscope, to find a ratio of crystal deposition of 10%.

Examples 16 to 26 and Comparative Examples 3 to 7

Coating liquids of liquid crystalline compositions were prepared in the same way as in Example 16, except that the compositions listed in Table 3 below were used in place of the composition of Example 1, and the ratio of crystal deposition was measured. Results were as summarized in Table 3 below.

TABLE 3

|  | The liquid crystal composition of the present invention | Crystal deposition |
|---|---|---|
| Example 16 | Example 1 | 3 |
| Example 17 | Example 2 | 3 |

TABLE 3-continued

| | The liquid crystal composition of the present invention | Crystal deposition |
|---|---|---|
| Example 18 | Example 3 | 3 |
| Example 19 | Example 4 | 3 |
| Example 20 | Example 5 | 3 |
| Example 21 | Example 6 | 3 |
| Example 22 | Example 7 | 2 |
| Example 23 | Example 8 | 3 |
| Example 24 | Example 9 | 3 |
| Example 25 | Example 10 | 2 |
| Example 26 | Example 11 | 3 |
| Comparative Example 3 | Comparative Composition (1') | 1 |
| Comparative Example 4 | Comparative Composition (2') | 1 |
| Comparative Example 5 | Comparative Composition (3') | 1 |
| Comparative Example 6 | Comparative Composition (4') | 1 |
| Comparative Example 7 | Comparative Composition (5') | 1 |

In Table 3 above, the ratio of crystal deposition was assigned with "3" if the area of crystal deposition visually accounts for 0 to 20% of the coated film, assigned with "2" for 20% to 50%, and assigned with "1" if exceeds 50%.

Example 96

<Preparation of Polymerizable Composition>

Using the composition of Example 84, a coating liquid (A) of liquid crystalline composition was prepared according to the compositional ratio below:

| Composition of Example 84 | 100 parts by mass |
|---|---|
| MEK | 233 parts by mass |

(Evaluation of Suppressive Effect on Crystal Deposition)

An arbitrary region of the surface of the liquid crystal film, in the thus obtained coated film of Example 96, was visually observed under a polarizing microscope, to find a ratio of crystal deposition of 5%.

Examples 97 to 107

Coating liquids of liquid crystalline compositions were prepared in the same way as in Example 1, except that the compositions listed in Table 4 below were used in place of the composition of Example 1, and the ratio of crystal deposition was measured. Results were as summarized in Table 4 below.

TABLE 4

| | The liquid crystal composition of the present invention | Crystal deposition |
|---|---|---|
| Example 96 | Example 84 | 3 |
| Example 97 | Example 85 | 2 |
| Example 98 | Example 86 | 3 |
| Example 99 | Example 87 | 3 |
| Example 100 | Example 88 | 3 |
| Example 101 | Example 89 | 3 |
| Example 102 | Example 90 | 2 |
| Example 103 | Example 91 | 3 |
| Example 104 | Example 92 | 3 |
| Example 105 | Example 93 | 3 |
| Example 106 | Example 94 | 3 |
| Example 107 | Example 95 | 3 |

In Table 4 above, the ratio of crystal deposition was assigned with "3" if the area of crystal deposition visually accounts for 0 to 20% of the coated film, assigned with "2" for 20% to 50%, and assigned with "1" if exceeds 50%.

[Chemical Formula 23]

Comparative composition (1')

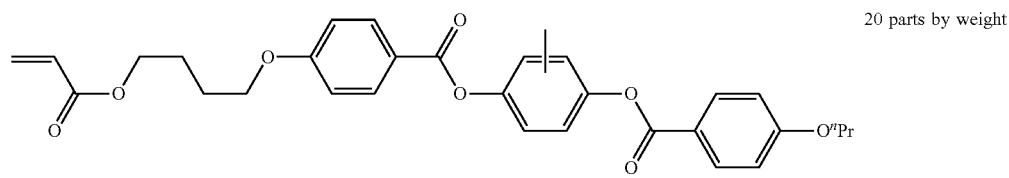

20 parts by weight

Compound (I-1)     80 parts by weight

-continued

[Chemical Formula 23]

Comparative composition (2')

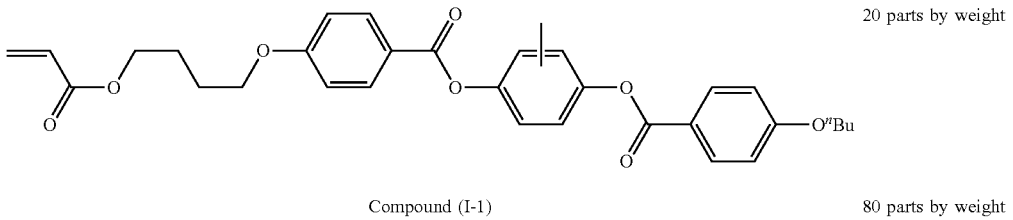

Compound (I-1)      20 parts by weight 80 parts by weight

Comparative composition (3')

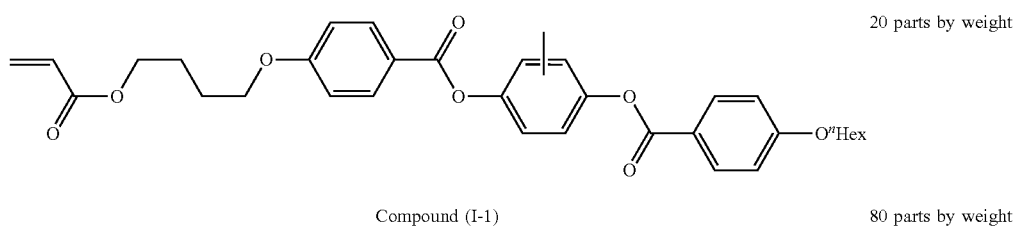

20 parts by weight

Compound (I-1)      80 parts by weight

Comparative composition (4')

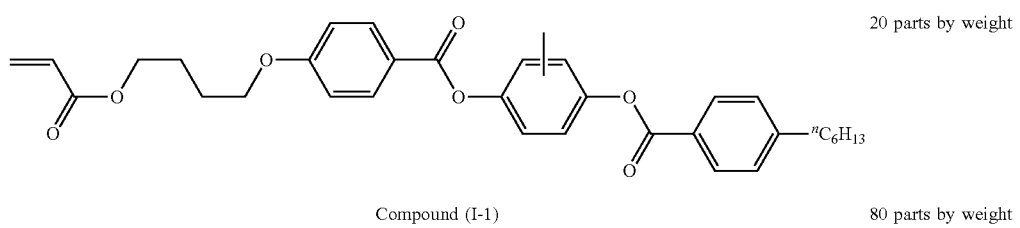

20 parts by weight

Compound (I-1)      80 parts by weight

Comparative composition (5')

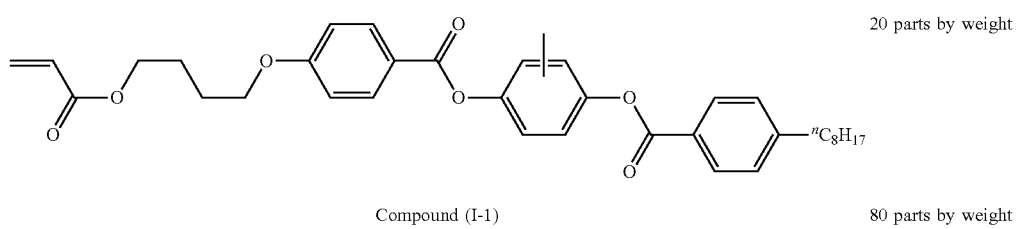

20 parts by weight

Compound (I-1)      80 parts by weight

Twenty parts by mass of compound used in Comparative Compositions (1') to (5') is a mixture of two isomers, and

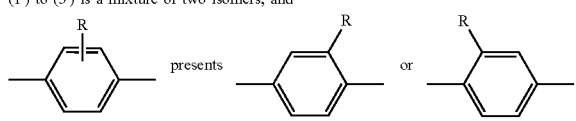

It was found from the results of Examples 16 to 26 and Comparative Examples 3 to 7, that the liquid crystal composition obtained in the individual Examples were superior to the liquid crystal compositions using the conventional polymerizable liquid crystal compounds in terms of suppressive effect on crystallization.

Example 51

<Fabrication of Selective Reflection Film>

A coating liquid (B) of liquid crystalline composition was prepared using the composition of Example 6, according to the method below.

| | |
|---|---|
| Composition of Example 6 | 100 parts by mass |
| Paliocolor LC756, chiral agent (from BASF) | 3 parts by mass |
| Air interface aligning agent (X1-1) | 0.04 parts by mass |
| IRGACURE 819, polymerization initiator (from BASF) | 3 parts by mass |
| Chloroform, solvent | 300 parts by mass |

[Chemical Formula 24]
Air Interface Aligning Agent

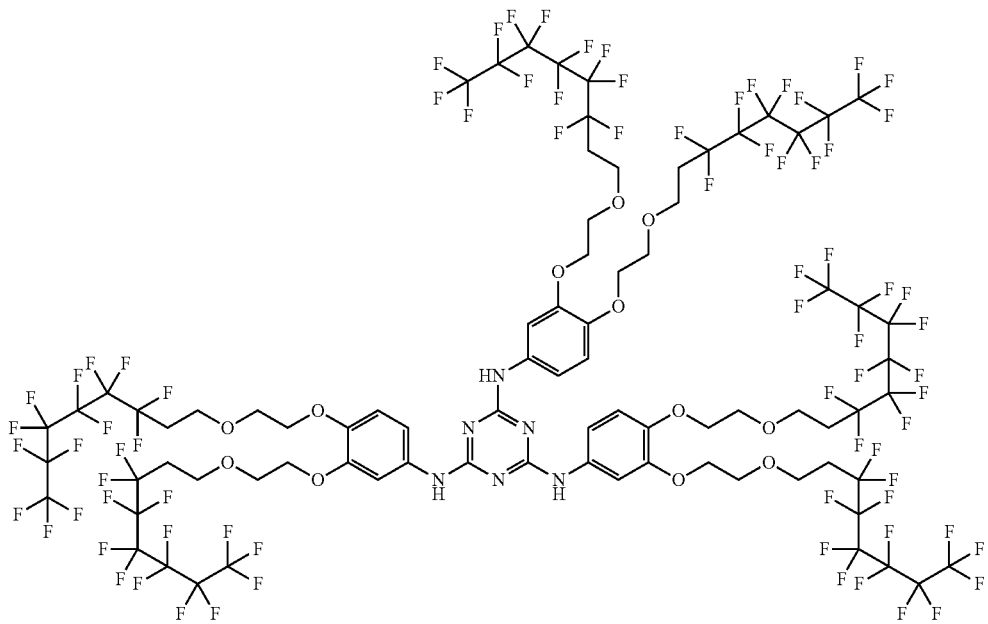

(X1-1)

On the surface of the alignment film of the substrate with alignment film manufactured in the same way as in Example 16, the coating liquid (B) of liquid crystal composition was coated at room temperature by spin coating, the coating was aged for alignment at 120° C. for 3 minutes, irradiated with light at room temperature using a high-pressure mercury lamp, with short wavelength UV components cut off, for 10 seconds to fix the alignment, to thereby obtain a selective reflection film. No crystal deposition in the coated film was observed over the period after the coating and before the heating.

The obtained selective reflection film was observed under a polarizing microscope, and was found to show uniform alignment without alignment defect. Further analysis of transmission spectrum using a spectrophotometer UV-3100PC from Shimadzu Corporation showed a selective reflection peak in the infrared region.

Examples 52 to 61

Coating liquids of liquid crystalline compositions were respectively prepared in the same way as in Example 51, except that the compositions of Examples 1 to 5, and Examples 7 to 11 were used in place of the composition of Example 6. These coating liquids were used to respectively form the selective reflection films in the same way as in Example 51. All of these selective reflection films showed good alignability. Measurement of transmission spectra using the spectrophotometer UV-3100PC showed selective reflection peaks in the infrared region.

Examples 108 to 119

Coating liquids of liquid crystalline compositions were respectively prepared in the same way as in Example 51, except that the compositions of Examples 84 to 95 were used in place of the composition of Example 6. These coating liquids were used to respectively form the selective reflection films in the same way as in Example 51. All of these selective reflection films showed good alignability. Measurement of transmission spectra using the spectrophotometer UV-3100PC showed selective reflection peaks in the infrared region.

Example 62

<Fabrication of Optical Compensation Film (1)>

A coating liquid (C) of liquid crystalline composition was prepared using the composition of Example 1, according to the method below.

| | |
|---|---|
| Composition of Example 1 | 100 parts by mass |
| IRGACURE 819, polymerization initiator (from BASF) | 3 parts by mass |
| Air interface aligning agent (X1-2) | 0.1 parts by mass |
| Methyl ethyl ketone, solvent | 400 parts by mass |

[Chemical Formula 25]
Air Interface Aligning Agent

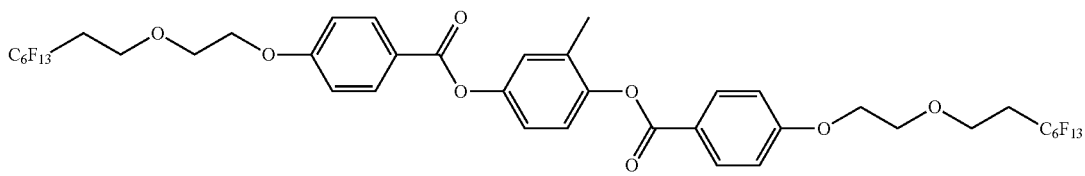

(X1-2)

On a cleaned glass substrate, polyimide alignment film SE-130 from Nissan Chemical Industries, Ltd. was formed by spin coating, dried, and baked at 250° C. for one hour. The obtained film was rubbed to thereby manufacture a substrate with alignment film. Over the surface of the substrate, the coating liquid (C) of liquid crystalline composition was coated at room temperature by spin coating, the coating was aged for alignment at 60° C. for one minute, irradiated with light at room temperature using a high-pressure mercury lamp, with short wavelength UV components cut off, for 10 seconds to fix the alignment, to thereby obtain an optical compensation film. No crystal deposition in the coated film was observed over the period after the coating and before the heating.

The obtained optical compensation film was observed under a polarizing microscope, and was found to show uniform alignment without alignment defect.

Further measurement of retardation (Re) of the obtained optical compensation film, using AxoScan (Mueller matrix polarimeter) from Axometrics, Inc., showed an Re(550) at 550 nm of 156.2 nm.

Examples 63 to 72

Coating liquids of liquid crystalline compositions were respectively prepared in the same way as in Example 62, except that the compositions of Examples 2 to 11 were used in place of the composition of Example 1. These coating liquids were used to respectively form the optical compensation films in the same way as in Example 62. The obtained optical compensation films were respectively observed under a polarizing microscope, and were found to show uniform alignment without alignment defect. Measured values of Re at 550 nm and thickness of the optical compensation films were as summarized below.

TABLE 5

| | The liquid crystal composition of the present invention | Re (nm) | Thickness (μm) |
|---|---|---|---|
| Example 62 | Example 1 | 156.2 | 0.98 |
| Example 63 | Example 2 | 157.1 | 0.98 |
| Example 64 | Example 3 | 156.9 | 0.97 |
| Example 65 | Example 4 | 191.8 | 1.01 |
| Example 66 | Example 5 | 179.5 | 0.99 |
| Example 67 | Example 6 | 173.6 | 1.00 |
| Example 68 | Example 7 | 162.8 | 1.00 |
| Example 69 | Example 8 | 160.1 | 0.98 |
| Example 70 | Example 9 | 160.3 | 1.02 |
| Example 71 | Example 10 | 161.6 | 0.98 |
| Example 72 | Example 11 | 158.0 | 0.99 |

Examples 120 to 131

Coating liquids of liquid crystalline compositions were respectively prepared in the same way as in Example 62, except that the compositions of Examples 84 to 95 were used in place of the composition of Example 1. These coating liquids were used to respectively form the optical compensation films in the same way as in Example 62. The obtained optical compensation films were respectively observed under a polarizing microscope, and were found to show uniform alignment without alignment defect. Measured values of Re at 550 nm and thickness of the optical compensation films were as summarized below.

TABLE 6

| | The liquid crystal composition of the present invention | Re (nm) | Thickness (μm) |
|---|---|---|---|
| Example 120 | Example 84 | 177.9 | 1.01 |
| Example 121 | Example 85 | 160.4 | 0.99 |
| Example 122 | Example 86 | 158.5 | 1.01 |
| Example 123 | Example 87 | 172.3 | 1.00 |
| Example 124 | Example 88 | 162.7 | 0.98 |
| Example 125 | Example 89 | 132.1 | 1.00 |
| Example 126 | Example 90 | 172.5 | 0.99 |
| Example 127 | Example 91 | 156.4 | 1.01 |
| Example 128 | Example 92 | 177.9 | 1.02 |
| Example 129 | Example 93 | 167.2 | 0.98 |
| Example 130 | Example 94 | 171.2 | 0.98 |
| Example 131 | Example 95 | 176.6 | 1.01 |

Example 73

<Fabrication of Optical Compensation Film (2)>

A coating liquid (D) of liquid crystalline composition was prepared using the composition of Example 1, according to the method below.

| | |
|---|---|
| Composition of Example 1 | 100 parts by mass |
| IRGACURE 907, polymerization initiator (from BASF) | 3 parts by mass |
| Sensitizer (Kayacure DETX, from Nippon Kayaku Co., Ltd.) | 1 part by mass |
| Air interface aligning agent (X1-3) | 0.11 parts by mass |
| Onium salt (X1-4) | 1.5 parts by mass |
| Methyl ethyl ketone, solvent | 300 parts by mass |

[Chemical Formula 26]
Air Interface Aligning Agent (XI-3)

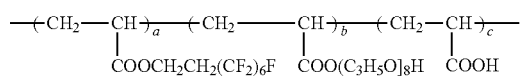

a = 40 b = 55 c = 5

[Chemical Formula 27]
Onium Salt (X1-4)

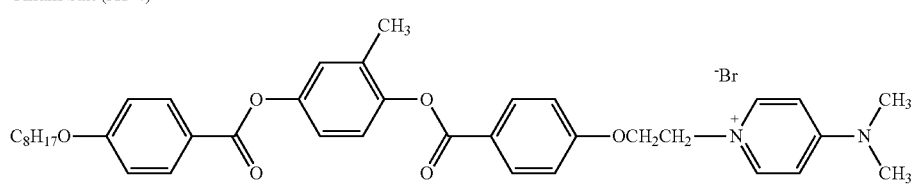

Compositional Ratio of Coating Liquid of Alignment Film Modified Polyvinyl alcohol, shown below 10 parts by mass

| Water | 371 parts by mass |
|---|---|
| Methanol | 119 parts by mass |
| Glutaraldehyde | 0.5 parts by mass |

[Chemical Formula 28]
Modified Polyvinyl Alcohol

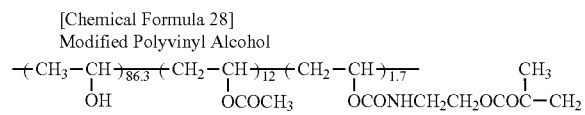

On a cleaned glass substrate, the coating liquid of alignment film described above was coated using a wire bar coater in an amount of 20 ml/m$^2$, dried at 60° C. under hot air for 60 seconds, and further at 100° C. under hot air for 120 seconds, to thereby manufacture a substrate with alignment film. Over the surface of the substrate, the coating liquid (D) of liquid crystalline composition was coated at room temperature by spin coating, the coating was aged for alignment at 60° C. for one minute, irradiated with light at 50° C. using a high-pressure mercury lamp, with short wavelength UV components cut off, for 10 seconds to fix the alignment, to thereby obtain an optical compensation film. No crystal deposition in the coated film was observed over the period after the coating and before the heating.

The obtained optical compensation film was observed under a polarizing microscope, and was found to show uniform alignment without alignment defect.

Further measurement of Rth of the obtained optical compensation film, using AxoScan (Mueller matrix polarimeter) from Axometrics, Inc., showed an Rth at 550 nm of −123.1 nm.

Examples 74 to 83

Coating liquids of liquid crystalline compositions were respectively prepared in the same way as in Example 73, except that the compositions of Examples 2 to 11 were used in place of the composition of Example 1. These coating liquids were used to respectively form the optical compensation films in the same way as in Example 73. The obtained optical compensation films were respectively observed under a polarizing microscope, and were found to show uniform alignment without alignment defect. Measured values of Rth at 550 nm and thickness of the optical compensation films were as summarized below.

TABLE 7

| | The liquid crystal composition of the present invention | Rth (nm) | Thickness (μm) |
|---|---|---|---|
| Example 73 | Example 1 | −123.1 | 1.42 |
| Example 74 | Example 2 | −122.9 | 1.48 |
| Example 75 | Example 3 | −123.5 | 1.52 |
| Example 76 | Example 4 | −153.4 | 1.49 |
| Example 77 | Example 5 | −141.6 | 1.47 |
| Example 78 | Example 6 | −137.5 | 1.51 |
| Example 79 | Example 7 | −128.7 | 1.50 |
| Example 80 | Example 8 | −125.8 | 1.50 |
| Example 81 | Example 9 | −126.3 | 1.50 |

TABLE 7-continued

| | The liquid crystal composition of the present invention | Rth (nm) | Thickness (μm) |
|---|---|---|---|
| Example 82 | Example 10 | −124.1 | 1.48 |
| Example 83 | Example 11 | −125.1 | 1.49 |

Examples 132 to 143

Coating liquids of liquid crystalline compositions were respectively prepared in the same way as in Example 73, except that compositions of Examples 84 to 95 were used in place of the composition of Example 1. These coating liquids were used to respectively form the optical compensation films in the same way as in Example 73. The obtained optical compensation films were respectively observed under a polarizing microscope, and were found to show uniform alignment without alignment defect. Measured values of Rth at 550 nm and thickness of the optical compensation films were as summarized below.

TABLE 8

| | The liquid crystal composition of the present invention | Rth (nm) | Thickness (μm) |
|---|---|---|---|
| Example 132 | Example 84 | −142.9 | 1.45 |
| Example 133 | Example 85 | −128.3 | 1.43 |
| Example 134 | Example 86 | −124.4 | 1.46 |
| Example 135 | Example 87 | −139.5 | 1.42 |
| Example 136 | Example 88 | −131.7 | 1.44 |
| Example 137 | Example 89 | −104.9 | 1.44 |
| Example 138 | Example 90 | −136.3 | 1.43 |
| Example 139 | Example 91 | −125.8 | 1.46 |
| Example 140 | Example 92 | −144.7 | 1.47 |
| Example 141 | Example 93 | −132.8 | 1.46 |
| Example 142 | Example 94 | −135.5 | 1.47 |
| Example 143 | Example 95 | −139.3 | 1.45 |

What is claimed is:

1. A method for manufacturing a liquid crystal composition, the method comprising concurrently obtaining a liquid crystal compound represented by the formula (I) below and a liquid crystal compound represented by the formula (II) below, by allowing a compound represented by the formula (III) below to react with a carboxylic acid represented by the formula (IV) below and a carboxylic acid represented by the formula (V) below;

$P^1$-$Sp^1$-$T^1$-$A^1$-B-$A^2$-$T^1$-$Sp^1$-$P^1$        Formula (I)

$P^1$-$Sp^1$-$T^1$-$A^1$-B-$A^3$-$T^2$-X        Formula (II)

$HY^1$—B—$Y^2$H        Formula (III)

$P^1$-$Sp^1$-$T^1$-COOH        Formula (IV)

X-$T^2$-COOH        Formula (V)

wherein, $P^1$ represents a polymerizable group;

$Sp^1$ represents a $C_{3-12}$ divalent aliphatic group which may have a substituent, and one $CH_2$ or two or more non-adjacent ($CH_2$)s in the aliphatic group may be substituted by —O—, —S—, —OCO—, —COO— or —OCOO—;

$T^1$ represents a 1,4-phenylene group;

$T^2$ represents a divalent group having a single bond or cyclic structure;

A¹ represents —COO—, —CONR¹— or —COS—, wherein R¹ represents a hydrogen atom or methyl group;

each of A² and A³ independently represents —OCO—, —NR¹CO— or —SCO—; wherein R¹ represents a hydrogen atom or methyl group;

B represents a divalent group having a cyclic structure which may have a substituent;

X represents a hydrogen atom, branched or straight-chain $C_{1-12}$ alkyl group, branched or straight-chain $C_{1-12}$ alkoxy group, phenyl group, cyano group, halogen atom, nitro group, acetyl group, vinyl group, formyl group, —OC(=O)R, wherein R represents a $C_{1-12}$ alkyl group, N-acetylamide group, acryloylamino group, N,N-dimethylamino group, N-maleimide group, methacryloylamino group, aryloxy group, N-alkyloxycarbamoyl group having a $C_{1-4}$ alkyl group, allyloxycarbamoyl group, N-(2-methacryloyloxyethyl)carbamoyloxy group, N-(2-acryloyloxyethyl)carbamoyloxy group or a structure represented by the Formula (V-I) below;

each of Y¹ and Y² independently represents O, NR¹, wherein R¹ represents a hydrogen atom or methyl group, or S;

-A⁴-T⁴-Sp²-P²    Formula (V-I)

wherein, P² represents a polymerizable group or hydrogen atom, and each of A⁴, T⁴ and Sp² are independently the same as A², T² and Sp¹.

2. The method for manufacturing a liquid crystal composition of claim 1, wherein in the formulae (I) to (V), X represents a hydrogen atom, branched or straight-chain $C_{1-12}$ alkyl group, branched or straight-chain $C_{1-12}$ alkoxy group, phenyl group, cyano group, halogen atom, nitro group, acetyl group or vinyl group.

3. The method for manufacturing a liquid crystal composition of claim 1, further comprising;
activating the carboxylic acid represented by the formula (IV) and the carboxylic acid represented by the formula (V), by converting the carboxylic acids into a mixed acid anhydride or acid halide, wherein
subsequent to the activating, the compound represented by the formula (III) is allowed to react with the activated carboxylic acid represented by the formula (IV) and the activated carboxylic acid represented by the formula (V), in the presence of a base.

4. The method for manufacturing a liquid crystal composition of claim 1,
wherein feed ratio by mole of the carboxylic acid represented by the formula (IV) and the carboxylic acid represented by the formula (V) falls in the range from 75:25 to 99:1.

5. The method for manufacturing a liquid crystal composition of claim 1,
wherein production ratio by mole of the compound represented by the formula (I) and the compound represented by the formula (II) falls in the range from 50:50 to 98:2.

6. The method for manufacturing a liquid crystal composition of claim 1,
wherein compositional ratio by mass of the compound represented by the formula (I) and the compound represented by the formula (II), in the liquid crystal composition, falls in the range from 50:50 to 95:5.

7. The method for manufacturing a liquid crystal composition of claim 1, wherein B represents any one linking group selected from the group (VI) consisting of the linking groups below;

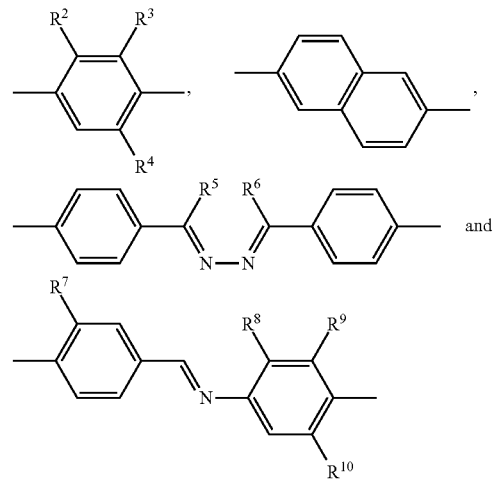

wherein, each of R² to R¹⁰ independently represents a hydrogen atom, branched or straight-chain $C_{1-4}$ alkyl group, branched or straight-chain $C_{1-4}$ alkoxy group, halogen atom, or, $C_{1-3}$ alkoxycarbonyl group.

8. The method for manufacturing a liquid crystal composition of claim 1, wherein T² represents any one linking group selected from the group (VII) consisting of the linking groups below;

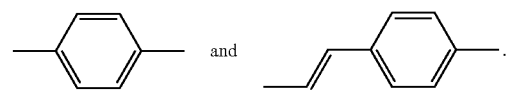

9. The method for manufacturing a liquid crystal composition of claim 1, wherein B represents any one linking group selected from the group (VIII) consisting of the linking groups below;

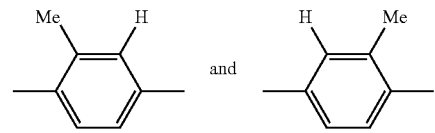

wherein Me is methyl group.

10. The method for manufacturing a liquid crystal composition of claim 1, wherein X represents a branched or straight-chain $C_{1-4}$ alkyl group, straight-chain $C_1$ or $C_2$ alkoxy group, or, phenyl group.

11. The method for manufacturing a liquid crystal composition of claim 1, wherein
each of Y¹ and Y² represents O,
A¹ represents —COO—, and
each of A² and A³ represents —OCO—.

* * * * *